(12) United States Patent
Rohr et al.

(10) Patent No.: US 10,058,267 B2
(45) Date of Patent: Aug. 28, 2018

(54) ANTENNA SUPPORT STRUCTURE FOR MAGNETIC RESONANCE IMAGING

(75) Inventors: Robert D. Rohr, LaOtto, IN (US); Christopher Salimes, Brookfield, WI (US); Leslie Wagner, Mukwonago, WI (US); Venkat Goruganti, Pewaukee, WI (US); Brian Brown, Wauwatosa, WI (US)

(73) Assignee: Neocoil, LLC, Pewaukee, WI (US)

( * ) Notice: Subject to any disclaimer, the term of this patent is extended or adjusted under 35 U.S.C. 154(b) by 1140 days.

(21) Appl. No.: 13/447,616

(22) Filed: Apr. 16, 2012

(65) Prior Publication Data

US 2012/0265053 A1    Oct. 18, 2012

Related U.S. Application Data

(60) Provisional application No. 61/475,884, filed on Apr. 15, 2011.

(51) Int. Cl.
| | |
|---|---|
| *A61B 5/055* | (2006.01) |
| *G01R 33/34* | (2006.01) |
| *G01R 33/3415* | (2006.01) |
| *A61B 5/00* | (2006.01) |

(52) U.S. Cl.
CPC ...... *A61B 5/0555* (2013.01); *G01R 33/34007* (2013.01); *G01R 33/3415* (2013.01); *G01R 33/34046* (2013.01); *A61B 5/0042* (2013.01); *A61B 2503/06* (2013.01)

(58) Field of Classification Search
CPC .......... G01R 33/3415; G01R 33/34046; G01R 33/341; A61B 5/0555; A61B 5/0042; A61B 2503/06
See application file for complete search history.

(56) References Cited

U.S. PATENT DOCUMENTS

| | | |
|---|---|---|
| 5,594,339 A | 1/1997 | Henderson et al. |
| 6,029,082 A | 2/2000 | Srinivasan et al. |
| 6,591,128 B1 | 7/2003 | Wu et al. |
| 6,611,702 B2 | 8/2003 | Rohling et al. |
| 6,650,926 B1 | 11/2003 | Chan et al. |
| 6,762,606 B2 | 7/2004 | Jevtic et al. |
| 6,867,593 B2 | 3/2005 | Menon et al. |
| 6,992,486 B2 | 1/2006 | Srinivasan |
| 7,378,846 B1 | 5/2008 | Damadian |

(Continued)

OTHER PUBLICATIONS

Keil et al., Size-Optimized 32-Channel Brain Arrays for 3 T Pediatric Imaging; Magn Reson Med. Dec. 2011; 66 (6); 1777-1787 (23 pages).

(Continued)

*Primary Examiner* — Elmer Chao
(74) *Attorney, Agent, or Firm* — Boyle Fredrickson, SC

(57) ABSTRACT

A patient support structure for use in a magnetic resonance image (MRI) scanner includes a base and a first and a second arm pivotally connected to the base. The patient support structure supports an anatomical region being imaged and positions an antenna array around the anatomical region. Access to the patient is improved by: providing a flexible coil that wraps around the anatomical region being imaged, providing a support structure open to the anterior region of the anatomical region being imaged, and providing a support structure that may be opened and closed about the anatomical region being imaged.

12 Claims, 15 Drawing Sheets

(56) References Cited

U.S. PATENT DOCUMENTS

| | | | |
|---|---|---|---|
| 7,599,728 B2 | 10/2009 | Feenan | |
| 7,602,190 B2 | 10/2009 | Piferi et al. | |
| 8,487,620 B2* | 7/2013 | Brown | A61B 5/0555 |
| | | | 324/318 |
| 2005/0113668 A1 | 5/2005 | Srinivasan | |
| 2007/0039101 A1* | 2/2007 | Luginbuhl | A61B 5/0555 |
| | | | 5/600 |
| 2008/0242957 A1* | 10/2008 | Gaspard | A61B 5/11 |
| | | | 600/301 |
| 2009/0088627 A1 | 4/2009 | Piferi et al. | |
| 2010/0094306 A1* | 4/2010 | Chang | A61B 17/7004 |
| | | | 606/90 |

OTHER PUBLICATIONS

Pediatric Coils—Achieva 3.0T Pediatric coils—Philips—(1 page).
AIRI—Neonatal Ventilator—Ideal for Transport/MRI—(1 page).
AIRI_HNS—Infant Head / Spine Array—(1 page).
AIRI_SIRI—Infant Cardiac Array—(1 page).
AIRI_SIRI_Peds_datasheet—Complete Solution for Infant Transport and MRI—(2 pages).

* cited by examiner

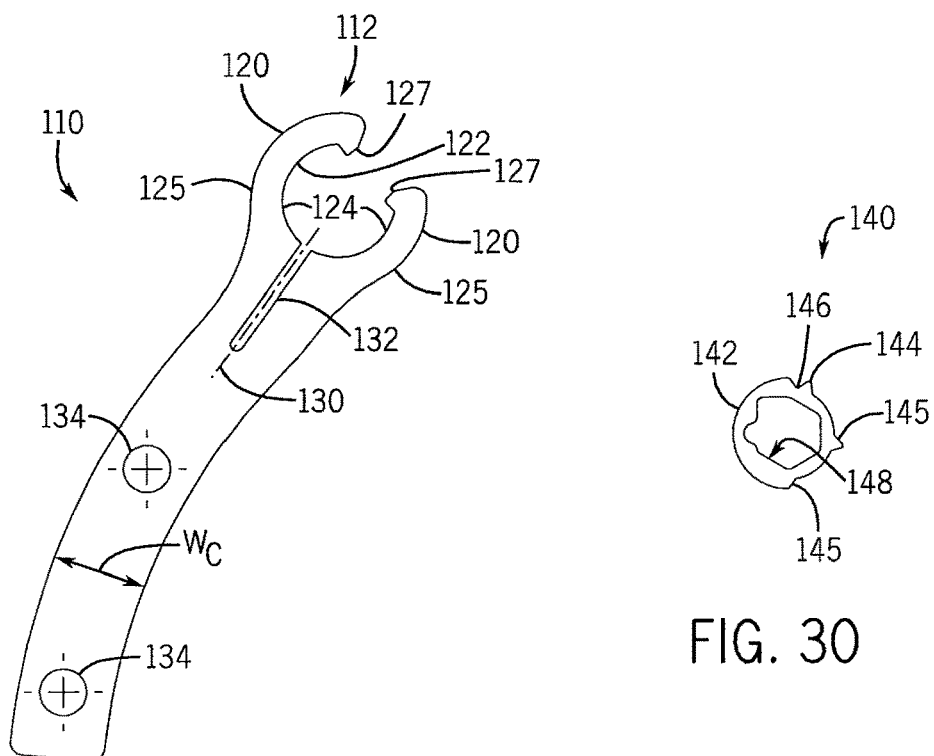
FIG. 29
FIG. 30
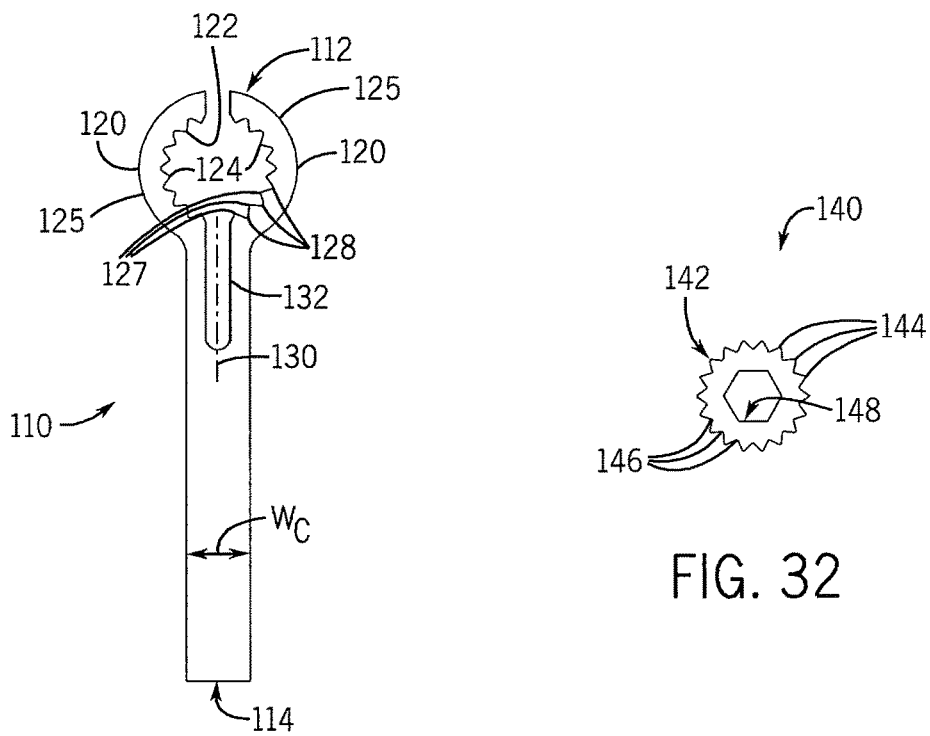
FIG. 31
FIG. 32

ANTENNA SUPPORT STRUCTURE FOR MAGNETIC RESONANCE IMAGING

CROSS-REFERENCE TO RELATED APPLICATIONS

This application claims priority to U.S. provisional application Ser. No. 61/475,884, filed Apr. 15, 2011, entitled Pediatric Imaging Assembly, the entire contents of which is incorporated herein by reference.

BACKGROUND OF THE INVENTION

The subject matter disclosed herein relates to a system for use in obtaining a magnetic resonance image (MRI) of a pediatric patient. More specifically, the assembly includes support structures both for patient comfort and stability as well as structures to position antenna arrays with respect to the patient.

As is known to those skilled in the art, obtaining MRIs of pediatric patients presents unique challenges. The quality of images obtained in MRI scanners is in part, a function of the location of the antenna array with respect to the anatomical region being images. Currently, most imaging systems are of a rigid or fixed construction, requiring different coils to be used for patients of different sizes. Because pediatric patients are generally smaller in size and present greater variation in the size of patients than adults, coils are not always properly sized for the patient. Further, due to the expense of coils and due to the majority of MRI patients being adults, it may be cost prohibitive for some imaging centers to maintain pediatric imaging assemblies.

Current systems on the market are made of rigid non-formable construction. Such systems limit the use of non-uniform shapes that must fit inside the predefined contour of the coil. These systems may also include a rigid mechanical latching system to secure the coil in position, which requires a person skilled in the equipment to release the latch in order to gain access to the patient.

Thus, it would be desirable to provide a MRI imaging assembly adaptable to varying sizes of patients and easily accessible to enhance imaging of pediatric patients.

BRIEF DESCRIPTION OF THE INVENTION

The subject matter disclosed herein describes an imaging assembly which includes a patient support structure and at least one imaging coil. More specifically, the imaging assembly is configured to facilitate pediatric imaging.

The patient support structure includes a recessed portion configured to receive an imaging coil such that a desired anatomical region of the patient may be placed on the imaging coil. The patient support structure further includes an exoskeleton configured to open and close anterior to the anatomy to be imaged, providing, for example, easy access to the face of a patient. In addition, the imaging coils may be used independently of the patient support structure for other imaging applications. Thus, the customers overall cost for imaging solutions is reduced.

The patient support structure according to one embodiment of the current invention adapts to non-uniform shapes and can be configured for patients of varying sizes to improve patient comfort. The anterior opening exoskeleton accommodates medical incubation and ventilation and allows quick and easy access by medical professionals to patients in the event of an emergency.

The patient support structure according to one embodiment of the current invention allows patient set up for precise patient placement and improved comfort by allowing the technician to adjust and maneuver the patient along with any external elements a patient may require in stepped fashion. The pivotal connector is configured to be easily positioned to a desired position for imaging, and openings in the structure permit viewing to the opposite side of the coil. Thus, the technician is able to position and access the patient from the top, front, back and one side of the coil, allowing improved patient comfort and positioning for imaging. The patient support structure further provides an audible click when opening and an audible click when properly closed. This frictional interfering engagement is robust enough to hold the coil in position and light enough to allow the coil to be readily opened without the need for depressing or deactivating a mechanical latch.

The patient support structure includes an exoskeleton with a c-clip insert system. The c-clip system is designed to fit into the exoskeleton as a separate component, but optionally may be integrally formed with the exoskeleton. The c-clip may be configured to provide an increased or reduced radial torque for placing the exoskeleton into a full closed or full open position. The c-clip further provides multiple latch and hold positions, easy field repair, and disassembly for cleaning and sanitizing. The exoskeleton may be designed with one or more arms.

According to one embodiment of the invention, the c-clip arm includes multiple position locating teeth. Each tooth on the c-clip arm is designed to cooperate with a corresponding tooth on the c-clip cam. C-clip jaws are designed and positioned to provide a resilient force sufficient to hold an arm of the exoskeleton in an aligned position relative to a base of the exoskeleton when the locating tooth of the arm and the corresponding tooth of the cam are engaged. The c-clip arm is curved to cooperate with the exoskeleton arm in proper assembly. Locating holes on the c-clip engage bosses on the exoskeleton to provide for correct radial alignment between the c-clip and the exoskeleton. A spring activation slot on the c-clip allows variation in the force required to position the arm. Increasing the slot width or depth will reduce the load force required to position the clip. Thus, the c-clip may be manufactured to provide differing positioning forces as needed to meet customer demands.

A cooperating cam includes a stop position engaging the locating tooth of the c-clip. The locating tooth butts against the stop position to limit radial positioning. A radial alignment portion of the cam is designed with a minimum clearance or slight interference condition to maintain concentricity between the c-clip and the cam during radial movement of the c-clip arm. The cam further includes an orientation and anti-rotation feature such that the cam may be used on any face of the exoskeleton base, eliminating the need for left or right orientated cams. The cam may be positioned on the base such that the orientation feature sets the left side radial position independently of the right side radial position. Optionally, the cam orientation and anti-rotation feature can be designed with a spline-type center, allowing the cam to be positioned such that the open and closed position are left or right of center as needed.

According to a first embodiment of the invention, a patient support structure for supporting an anatomical region of a patient and for positioning a flexible antenna array with respect to the anatomical region while obtaining a Magnetic Resonance Image (MRI) is disclosed. The patient support structure includes a base, a first arm, and a second arm. The base includes a first end, a second end opposite the first end, a first side, and a second side opposite the first side. Each of the first and second sides extend between the first and second ends. The base also includes at least one mounting surface proximate to the first side of the base and at least one mounting surface proximate to the second side of the base. The first arm includes a first end proximate to the base, a second end distal from the base, at least one mounting surface pivotally connected to the at least one mounting surface proximate to the first side of the base, and at least one antenna guide configured to slidably engage the flexible antenna array. The first arm is movable between a first position and a second position. The second arm includes a first end proximate to the base, a second end distal from the base, at least one mounting surface pivotally connected to the at least one mounting surface proximate to the second side of the base, and at least one antenna guide configured to slidably engage the flexible antenna array. The second arm is movable between a first position and a second position.

According to another aspect of the invention, a first friction mount may pivotally connect the mounting surface of the first arm to the mounting surface proximate to the first side of the base, and a second friction mount may pivotally connect the mounting surface of the second arm to the mounting surface proximate to the second side of the base. The base may include a channel extending between the first and second ends and configured to receive a member protruding from a surface of the antenna array. Optionally, the patient support structure further includes a riser block extending longitudinally between the first and second ends of the base and extending away from the base between the first and second arms. The riser block engages the antenna array to position the antenna array between the first and second arms.

According to still another aspect of the invention, the first arm may include an arcuate central support member, and the second arm may include an arcuate central support member. The antenna guide of the first and second arms each include a first retention member extending outward in a first direction from a center axis of the arcuate central support member proximate to the second end of the respective arm and a second retention member extending outward in a second direction, opposite the first direction, from the center axis of the arcuate central support member proximate to the first end of the respective arm. The first and second retention members of the first and second arms may each define a channel extending along the end of the retention member distal from the center axis of the arcuate central support member and extending generally parallel to the arcuate central support member.

According to yet another aspect of the invention, the antenna guide of the first arm may include a first channel extending along at least a portion of a first side of the first arm and a second channel extending along at least a portion of a second side of the first arm. The antenna guide of the second arm may include a first channel extending along at least a portion of a first side of the second arm and a second channel extending along at least a portion of a second side of the second arm. The base may include a planar lower surface. Optionally, the base may include an upper surface extending between the first end, the second end, the first side and the second side. The upper surface has a first side facing the first and second arms and a second side opposite the first side. A handle may protrude from the second side of the upper surface into a cavity defined by the first end, the second end, the first side, the second side and the upper surface.

According to another embodiment of the invention, a patient support structure for use with a Magnetic Resonance Image (MRI) scanner includes a base having a first end, a second end opposite the first end, a first side, a second side opposite the first side, and an upper surface defined generally by an upper edge of each of the first end, second end, first side, and second side. The patient support structure also includes a first mounting block protruding from the upper surface and extending generally parallel to and proximate with the first side of the base and a second mounting block protruding from the upper surface and extending generally parallel to and proximate with the second side of the base. Each of the first and second mounting blocks has a first end and a second end opposite the first end. The patient support structure also includes a first and a second arm. The first arm has a first end, a second end opposite the first end, a front wall, a rear wall opposite the front wall, and a curved side wall extending between at least a portion of an, outer edge of each of the front wall and the rear wall. The first end of the front wall is configured to pivotally mount to the first end of the first mounting block and the first end of the rear wall is configured to pivotally mount to the second end of the first mounting block. The second arm has a first end, a second end opposite the first end, a front wall, a rear wall opposite the front wall, and a curved side wall extending between at least a portion of an outer edge of each of the front wall and the rear wall. The first end of the front wall is configured to pivotally mount to the first end of the second mounting block, and the first end of the rear wall is configured to pivotally mount to the second end of the second mounting block. Each of the first and second arms also include an antenna array guide for positioning a flexible antenna array within the patient support structure.

According to another aspect of the invention, the antenna array guide for each of the first and second arms may include a first retaining surface extending from the front wall toward the center of the respective arm, along a portion of the length of the front wall. The first retaining surface is generally parallel to and offset from the curved side wall. The antenna array guide may also include a second retaining surface extending from the rear wall toward the center of the respective arm, along a portion of the length of the front wall. The first retaining surface is generally parallel to and offset from the curved side wall.

According to yet another aspect of the invention, the antenna array guide for each of the first and second arms may include a first retention member proximate to the second end of the respective arm extending outwardly from the front wall of the respective arm, and a second retention member proximate to the second end of the respective arm extending outwardly from the rear wall of the respective arm. Each retention member including a first surface extending from the respective front or rear wall, a retaining surface, offset from and generally parallel to the first surface, and an outer surface connecting the distal edge of each of the first surface and the retaining surface. A channel is formed by the first surface, retaining surface, and outer surface, where the channel slidably engages the antenna array.

According to still another aspect of the invention, the first arm is pivotally mounted to the first mounting block by a first friction mount and the second arm is pivotally mounted to the second mounting block by a second friction mount. The first friction mount may include at least one washer compressible between the front wall of the first arm and the first end of the first mounting block and at least one washer compressible between the rear wall of the first arm and the second end of the first mounting block, and the second friction mount includes at least one washer compressible between the front wall of the second arm and the first end of the second mounting block and at least one washer compressible between the rear wall of the second arm and the second end of the second mounting block. Optionally, each friction mount includes a clip and a cam. The clip is connected to the first end of the front or rear wall and includes a body mounted to the front or rear wall, a pair of arcuate members extending from the body and defining an opening therebetween, and a slot in communication with the opening and extending along at least a portion of a length of the body. The cam is connected to each end of the first and second mounting blocks and includes an outer periphery complementary to the opening defined between the arcuate members. The arcuate members are deflected apart by the outer periphery of the cam as each arm is rotated between a first and a second position.

According to yet another aspect of the present invention, a patient support structure for supporting an anatomical region of a patient and for positioning a flexible antenna array with respect to the anatomical region while obtaining a Magnetic Resonance Image (MRI) is disclosed. The patient support structure includes a base, a first arm including a first retention means to hold the flexible antenna array along the inner periphery of the first arm, a second arm including a second retention means to hold the flexible antenna array along the inner periphery of the second arm, a first friction mounting means to pivotally connect the first arm to the base, and a second friction mounting means to pivotally connect the second arm to the base.

These and other objects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWING(S)

Various exemplary embodiments of the subject matter disclosed herein are illustrated in the accompanying drawings in which like reference numerals represent like parts throughout, and in which.

Figure 5:
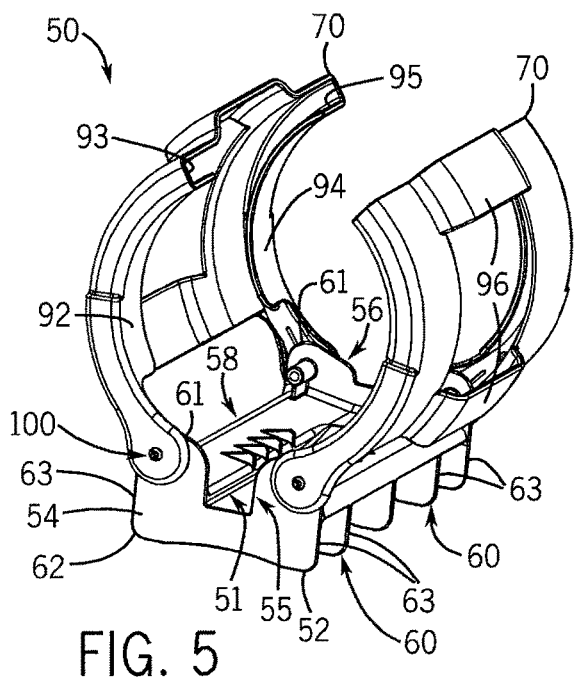
FIG. 5 is a perspective view of a curved patient support structure used in the patient support structure of HO shown in a home position.
Figure 6:
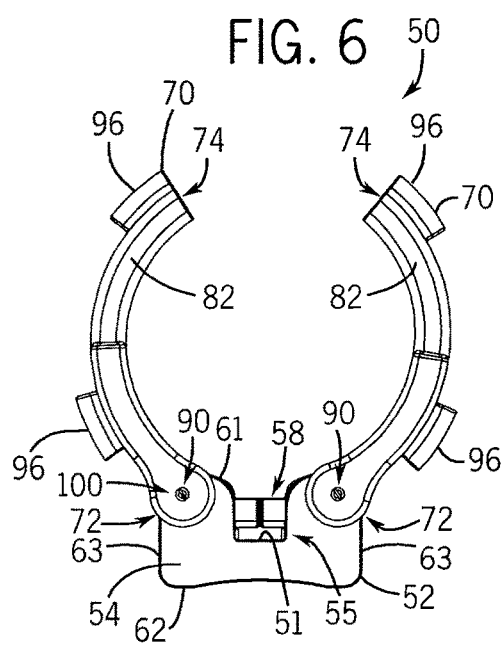
FIG. 6 is front elevation view of the curved patient support structure of FIG. 5.
Figure 7:
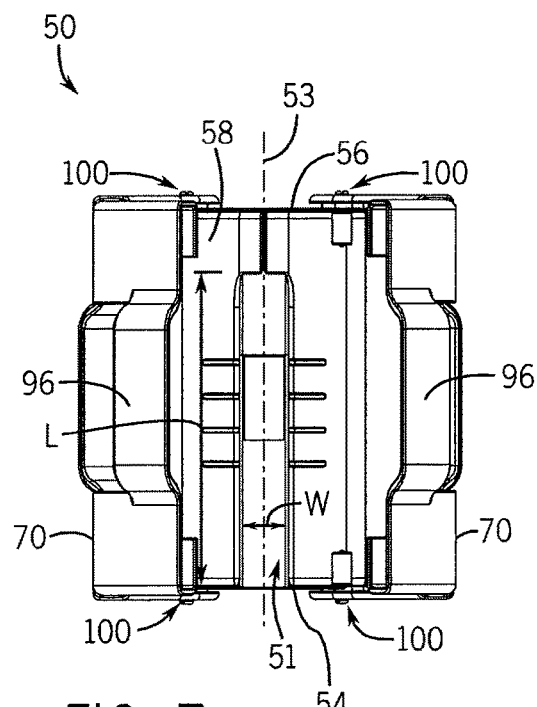
FIG. 7 is a top plan view of the curved patient support structure of FIG. 5.
Figure 8:
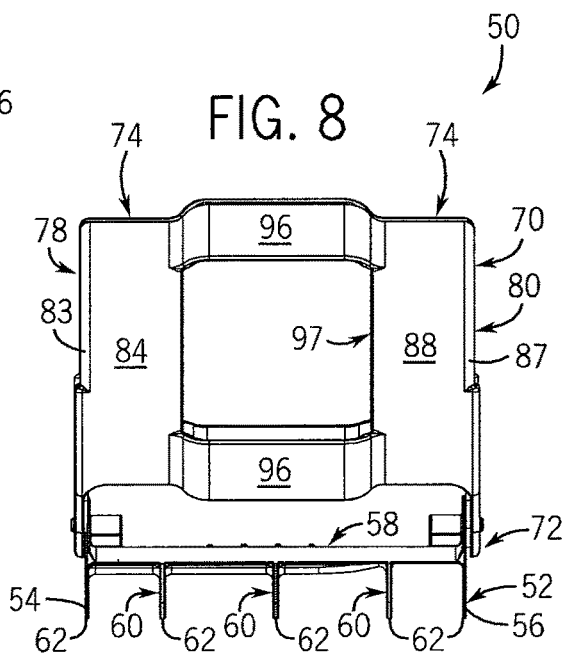
FIG. 8 is a side elevation view of the curved patient support structure of FIG. 5.
Figure 25:
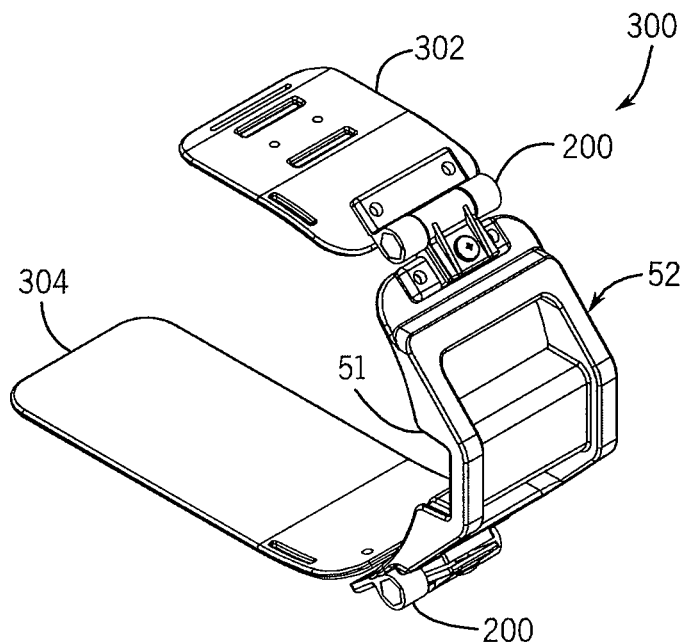
Figure 26:
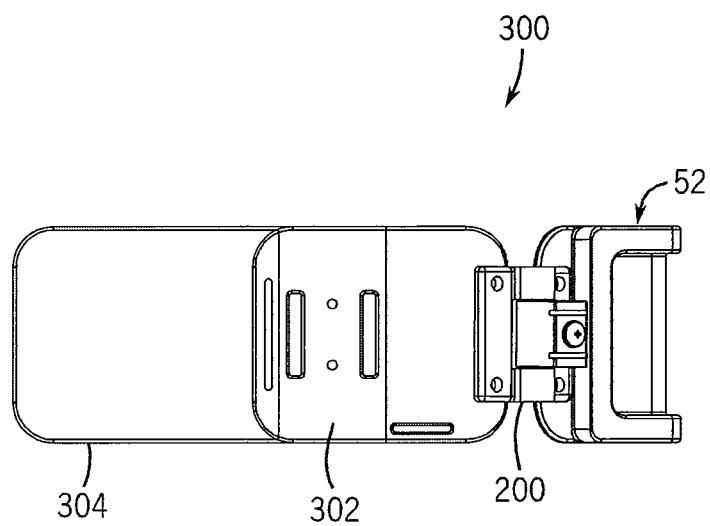
Figure 27:
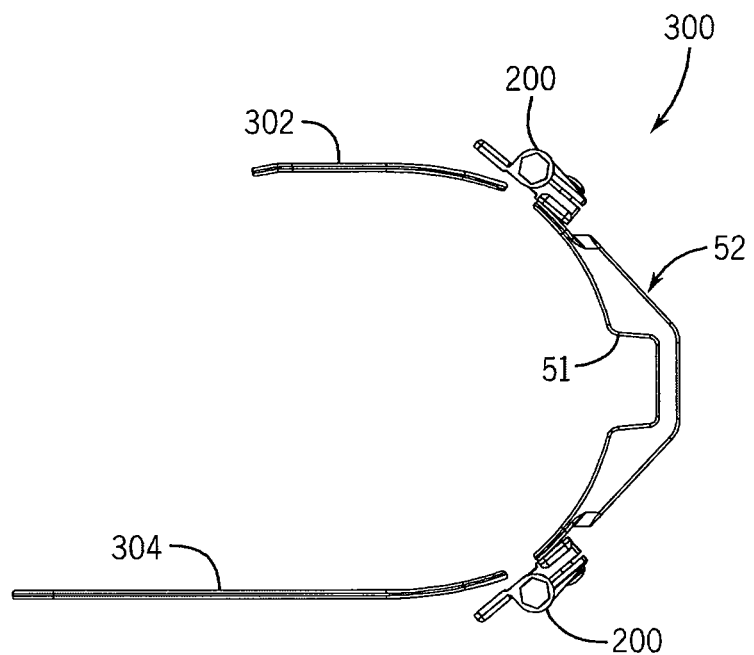
Figure 28:
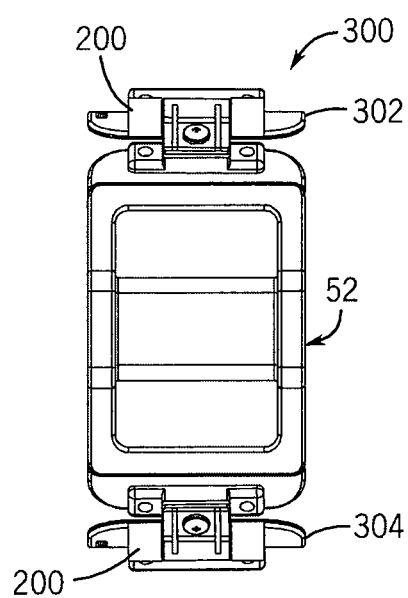
Figure 33:
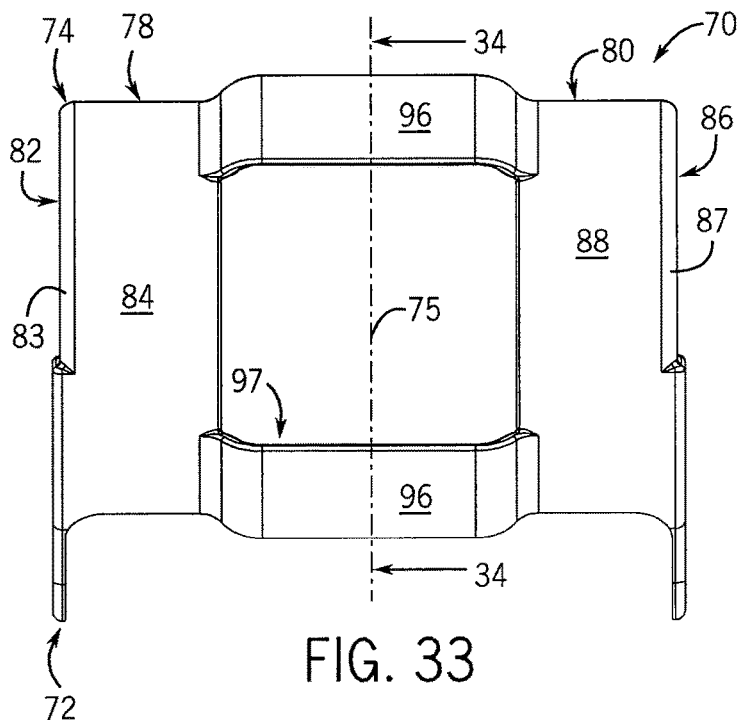
Figure 34:
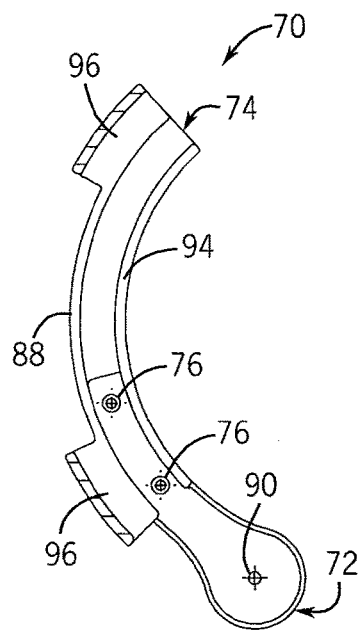
Figure 35:
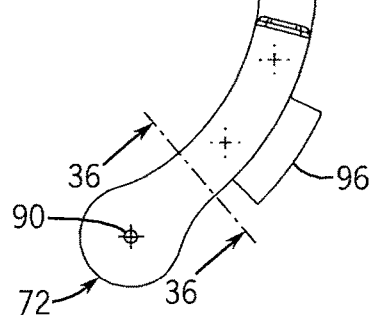
Figure 36:
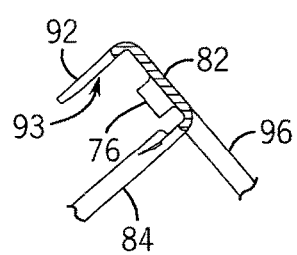
Figure 37:
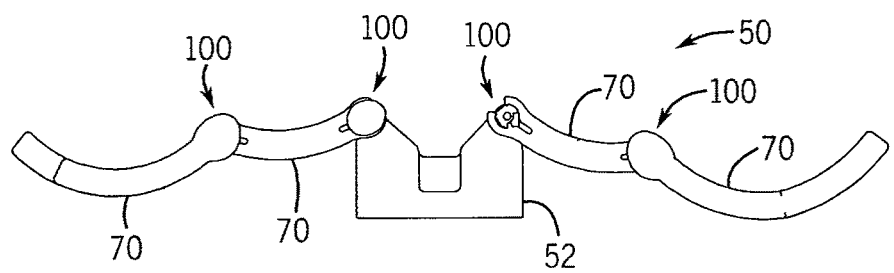
Figure 38:
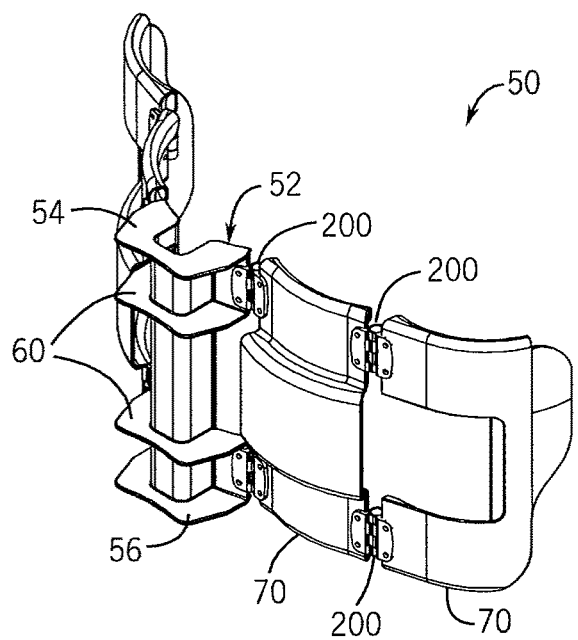
Figure 39:
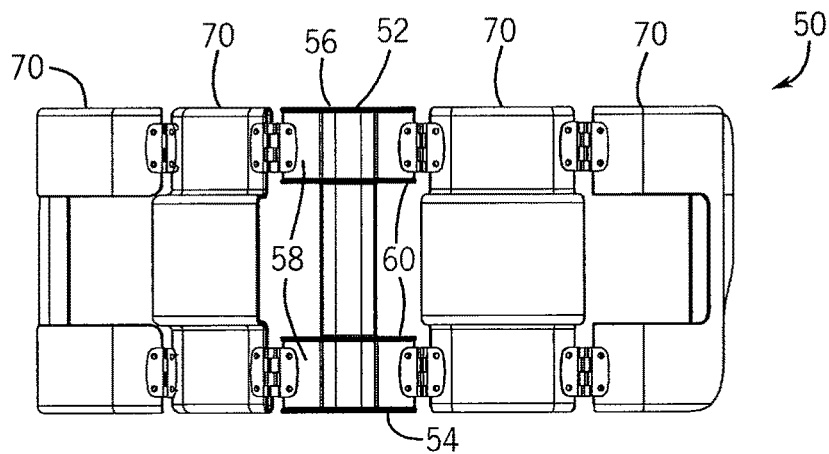
Figure 40:
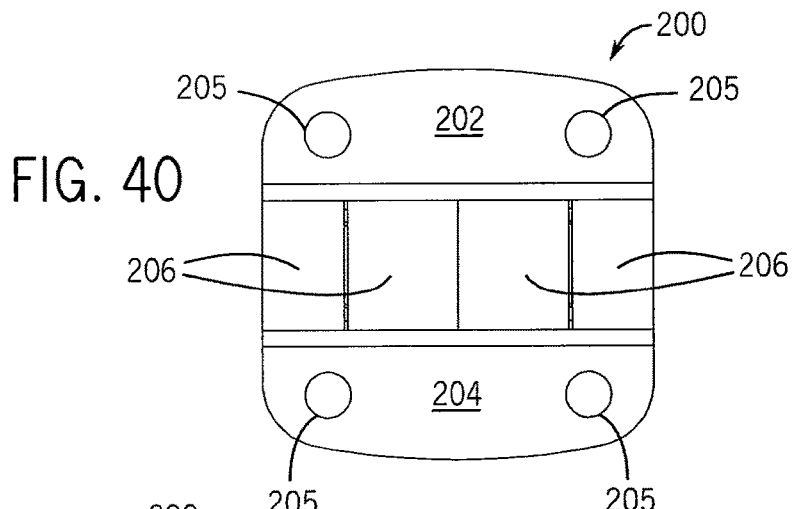
Figure 41:
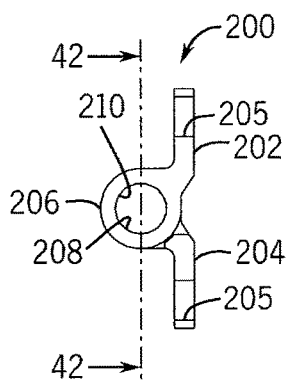
Figure 42:
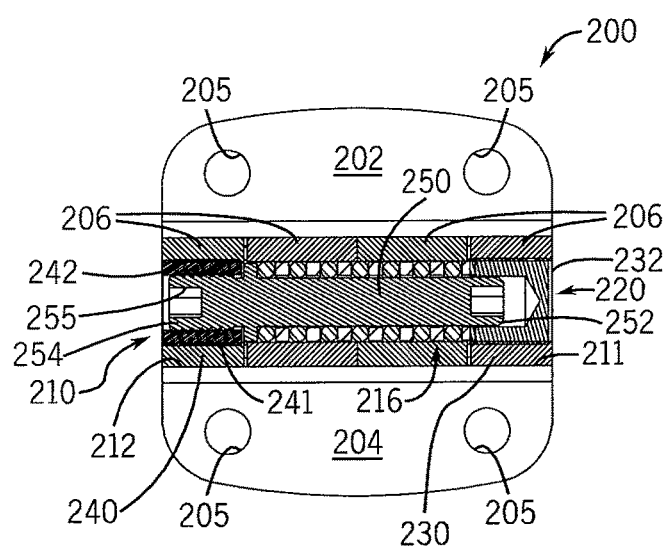
Figure 43:
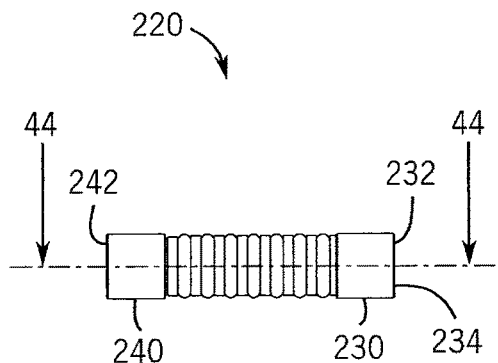
Figure 44:
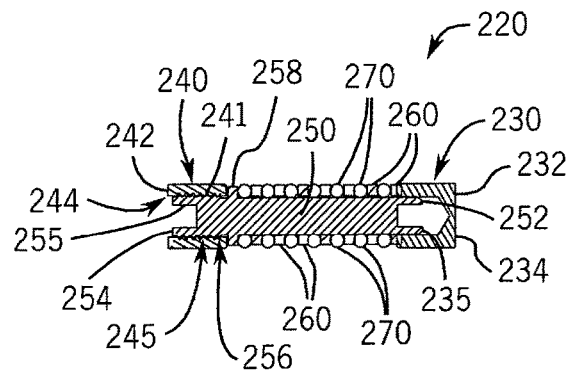
Figure 45:
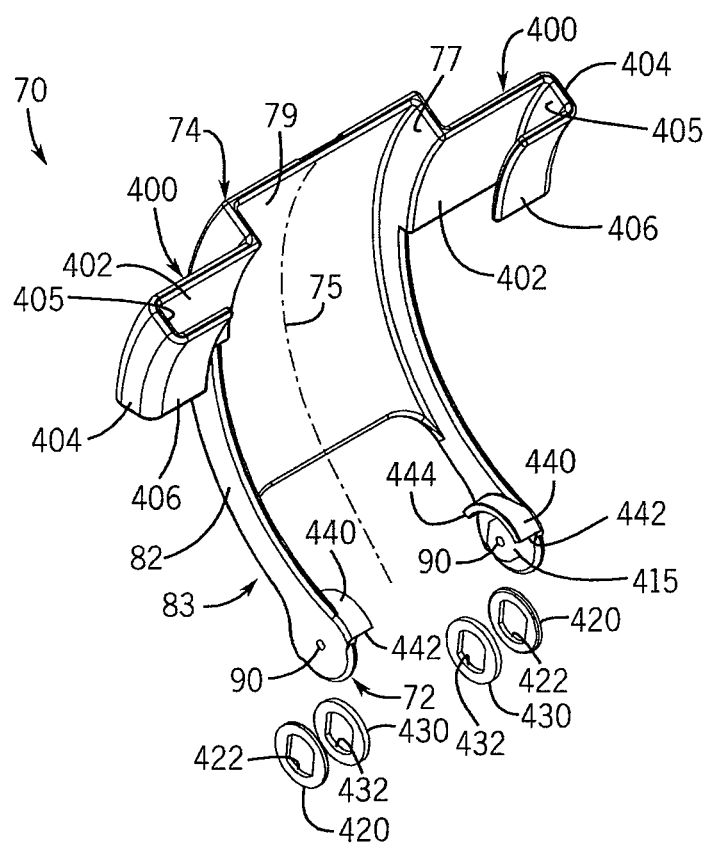
Figure 46:
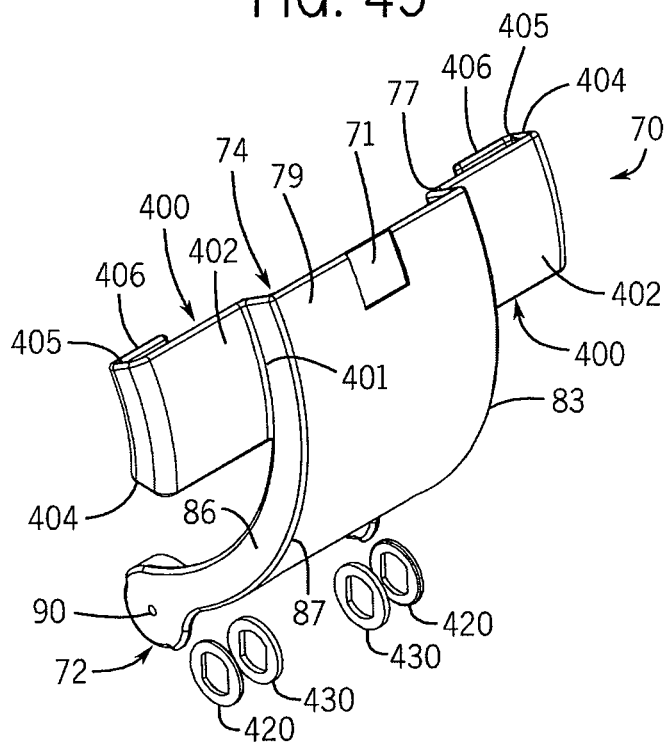

FIG. 25 a perspective view of a curved patient support structure according to another embodiment of the invention;

FIG. 26 is a top plan view of the curved patient support structure of FIG. 25;

FIG. 27 is a side elevation view of the curved patient support structure of FIG. 25;

FIG. 28 is front elevation view of the curved patient support structure of FIG. 25;

FIG. 29 is a front elevation view of one embodiment of a c-clip used in the curved patient support structure of FIG. 5;

FIG. 30 is a front elevation view of one embodiment of a cam used in cooperation with the c-clip of FIG. 29;

FIG. 31 is a front elevation view of another embodiment of a c-clip used in the curved patient support structure, of FIG. 5;

FIG. 32 is a front elevation view of one embodiment of a cam used in cooperation with the c-clip of FIG. 31;

FIG. 33 is a side elevation view of one embodiment of an arm used in the curved patient support structure of FIG. 5;

FIG. 34 is a cross-sectional view of the arm in FIG. 33 taken at 34-34;

FIG. 35 is a front elevation view the arm used in FIG. 33;

FIG. 36 is a partial cross-sectional view of the arm in FIG. 35 taken at 36-36;

FIG. 37 is a side elevation view of another embodiment of a curved patient support structure shown in a open position;

FIG. 38 is a perspective view of another embodiment of a curved patient support structure shown in a open position;

FIG. 39 is a bottom plan view of the curved patient support structure of FIG. 38;

FIG. 40 is a top plan view of a hinge used in the curved patient support structure of FIG. 38;

FIG. 41 is a side elevation view of the hinge of FIG. 40;

FIG. 42 is a cross-sectional view of the hinge of FIG. 41 taken at 42-42;

FIG. 43 is a front elevation view of the pin assembly for the hinge of FIG. 40;

FIG. 44 is a cross-sectional view of the pin assembly of FIG. 43 taken at 44-44;

FIG. 45 is a perspective view of another embodiment of an arm used in the curved patient support structure; and FIG. 46. is a reversed perspective view of the arm of FIG. 45.

In describing the preferred embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements where such connection is recognized as being equivalent by those skilled in the art.

DETAILED DESCRIPTION OF THE PREFERRED EMBODIMENTS

The various features and advantageous details of the subject matter disclosed herein are explained more fully with reference to the non-limiting embodiments described in detail in the following description.

Figure 1:
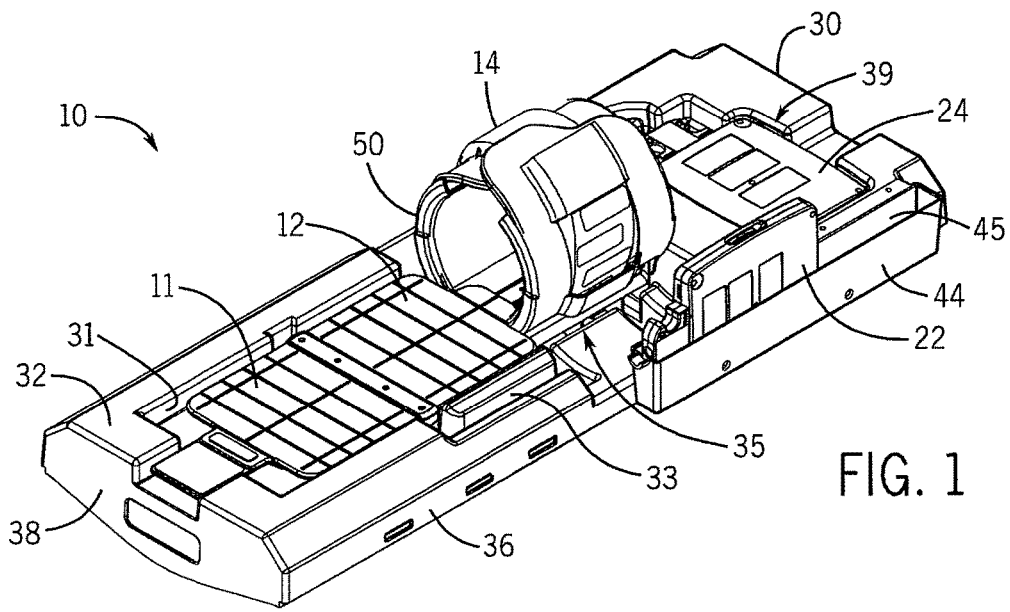
FIG. 1 is a perspective view of the patient support assembly according to one embodiment of the invention.
Figure 2:
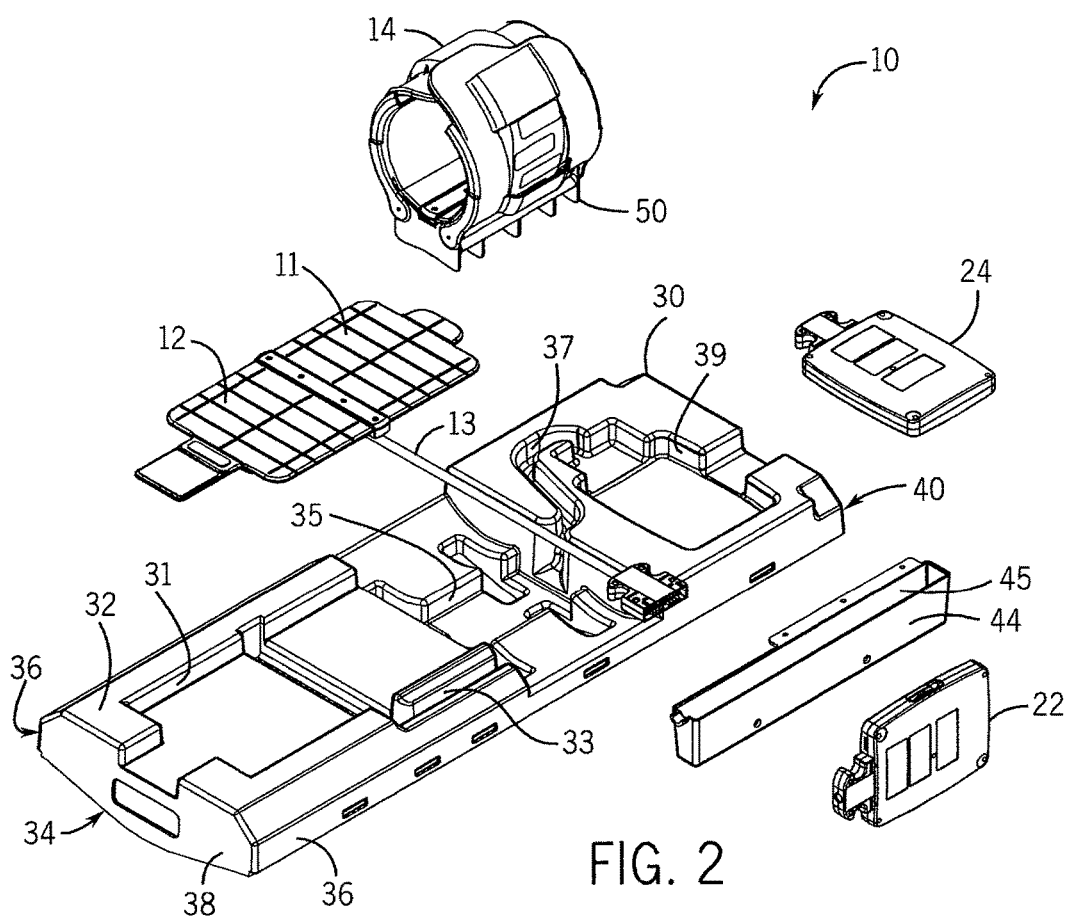
FIG. 2 is an exploded view of the patient support assembly of FIG. 1.

Turning initially to FIGS. 1 and 2, one embodiment of a patient support assembly 10 includes at least one patient stabilization structure used to position a patient within a MRI scanner. According to the illustrated embodiment, a first patient support 30 includes a top surface 32, a bottom surface 34, and multiple side walls 36, a front wall 38, and a rear wall 40 joining the top surface 32 and the bottom surface 34. The first patient support 30 may be a single molded assembly or, optionally, may include two or more components joined to form the first patient support 30.

The top surface 32 includes a first recess 31 configured to receive a first antenna array 12. The antenna array 12 may be, for example, an antenna array as provided by applicant and described in U.S. Pat. Pub. No. 2010/0315085, herein incorporated by reference. The depth of the first recess 31 is equal to or greater than the thickness of the first antenna array 12 such that a top surface 11 of the first antenna array 12 is at or below the top surface 32 of the first patient support 30. The walls of the recess 31 extending above the antenna array 12 may help position and/or retain a pediatric patient on the first patient support 30. For example, the top surface 32 of each wall may be formed to support the arms of a patient. A first channel 33 is in communication with the recess 31 and is configured to receive a cable 13 extending from the first antenna array 12 to the MRI scanner. A first preamplifier module 22 may be connected in series between the first antenna array 12 and the MRI scanner. Optionally, preamplifier circuits may be incorporated into the antenna array 12 and the cable 13 may be connected directly to the MRI scanner. The first preamplifier module 22 is supported within a cavity 45 of a tray 44 mounted to a side 36 of the first patient support 30. Optionally, the tray 44 may be integrally formed with the first patient support 30 and the cavity 45 may be another recessed portion of the first patient support 30. According to still another embodiment, if the electronic circuits of the first preamplifier module 22 are incorporated into the first antenna array 12, the tray 44 may be eliminated.

The top surface 32 includes a second recess 35 configured to receive a second patient support 50. The second patient support 50 may be used to support the head of a pediatric patient, and is also referred to herein as the head support 50. Optionally, the second patient support 50 may be used to support, for example, arms or legs of adult patients. The head support 50 is configured to support a second antenna array 14. A second channel 37 is in communication with the second recess 35 and is configured to receive a cable extending from the second antenna array 14 to the MRI scanner. A second preamplifier module 24 may be connected in series between the second antenna array 14 and the MRI scanner. Optionally, preamplifier circuits may be incorporated into the second antenna array 14 and the, cable may be connected directly to the MRI scanner. If the second preamplifier module 24 is included, a third recess 39 may be formed in the first patient support 30 and configured to receive the second preamplifier module 24. If the cable from the second antenna array 14 is connected directly to the MRI scanner, the third recess 39 may be eliminated.

The spatial relationship of the first recess 31 with respect to the second recess 35 is configured to provide improved image quality if both the first and second antenna arrays, 12 and 14 respectively, are used. Adjacent or overlapping antennas in the antenna arrays, 12 and 14, can cause coupling between the coils, degrading image quality. However, if the arrays, 12 and 14, are oriented properly with respect to each other, the coupling can be reduced or eliminated, providing improved image quality. Consequently, the first and second recesses, 31 and 35, are configured such that the first and second antenna arrays, 12 and 14, are oriented in a preferred alignment to minimize coupling between the arrays.

Figure 3:
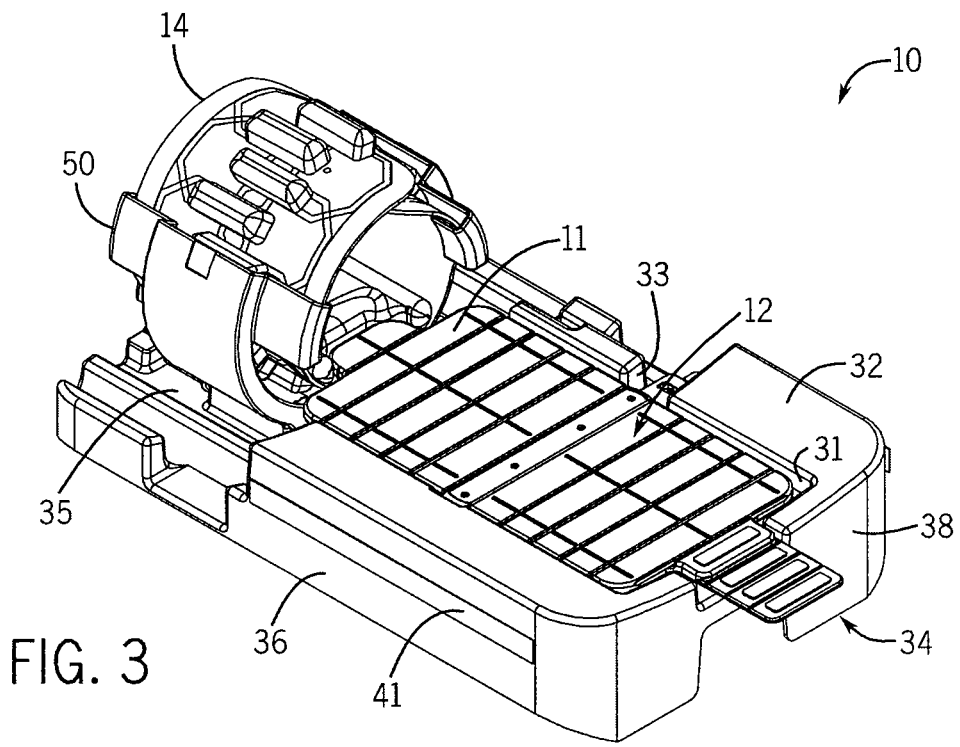
FIG. 3 is a perspective view of the patient support assembly according to another embodiment of the invention.
Figure 4:
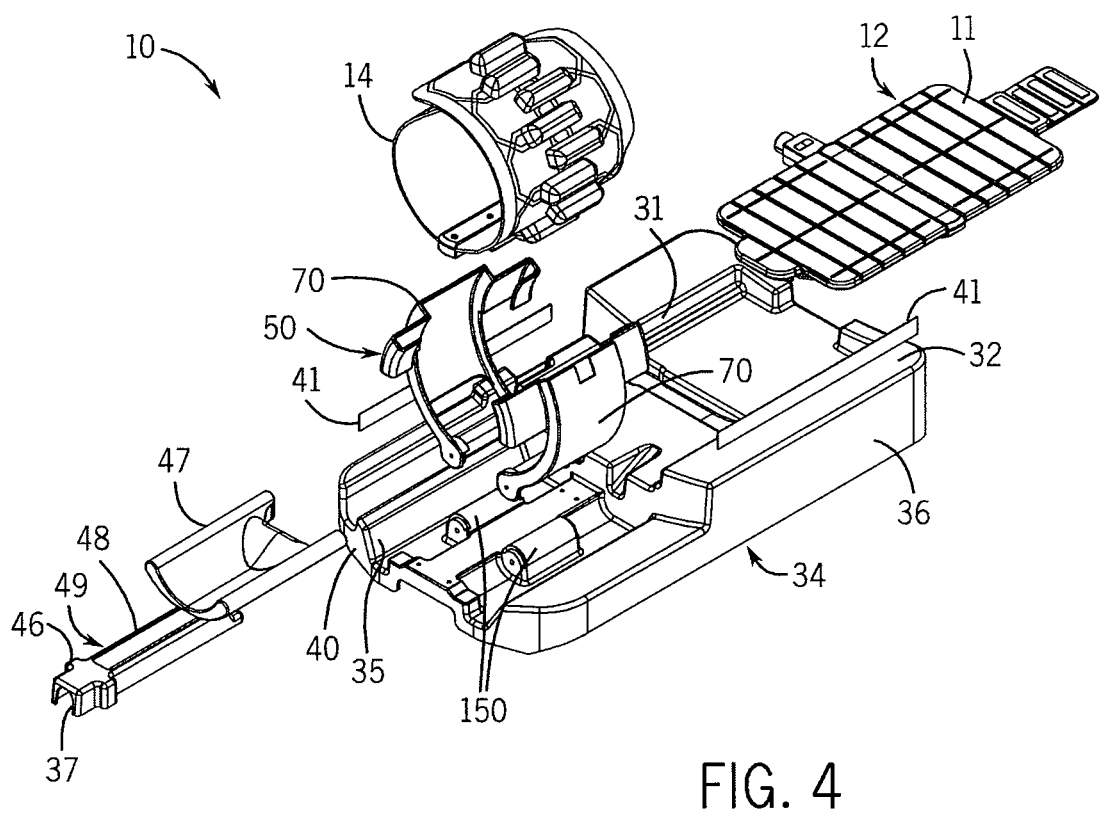
FIG. 4 is an exploded view of the patient support assembly of FIG. 3.

Referring next to FIGS. 3 and 4, another embodiment of a patient support assembly 10 includes at least one patient stabilization structure used to position a patient within a MRI scanner. According to the illustrated embodiment, a first patient support 30 includes a top surface 32, a bottom surface 34, and multiple side walls 36, a front wall 38, and a rear wall 40 joining the top surface 32 and the bottom surface 34. The first patient support 30 may be a single molded assembly or, optionally, may include two or more components joined to form the first patient support 30.

The top surface 32 includes a first recess 31 configured to receive a first antenna array 12. The depth of the first recess 31 is equal to or greater than the thickness of the first antenna array 12 such that a top surface 11 of the first antenna array 12 is at or below the top surface 32 of the first patient support 30. A first channel 33 is in communication with the recess 31 and is configured to receive a cable 13 extending from the first antenna array 12 to the MRI scanner.

The walls of the recess 31 extending above the antenna array 12 may help position and/or retain a pediatric patient on the first patient support 30. For example, the top surface 32 of each wall may be formed to support the arms of a patient. Optionally, it may be desirable to more firmly retain a patient to the support assembly 10 to prevent movement during imaging. A strip of material 41 made up of one side of a hook and loop fastener may be adhered along each side 36 of the patient support assembly 10. One or more straps (not shown) made up of the other side of the hook and loop fastener may engage the strip of material 41 along one side 36 of the patient support assembly 10, extend over the patient, and engage the strip of material 41 along the other side 36 of the patient support assembly 10.

The top surface 32 includes a second recess 35 configured to receive a second patient support 50. The second patient support 50 may be used to support the head of a pediatric patient, and is also referred to herein as the head support 50. Optionally, the second patient support 50 may be used to support, for example, arms or legs of adult patients. When the second patient support 50 is used to support the head of a patient, a contoured pad 47 may be inserted within the second patient support 50 to provide comfort and support for patient's head during the procedure. The head support 50 is configured to support a second antenna array 14. A riser 49 may placed between the pivot mounts 160 to which a first end 72 of each arm 70 is mounted. The riser 49 helps position the contoured pad 47 at a desired height to support the patient's head and defines the second channel 37 which is in communication with the second recess 35 and is configured to receive a cable extending from the second antenna array 14 to the MRI scanner. The riser 49 includes an opening 48 along an upper surface 46 configured to receive the spine of the antenna array 14.

Referring next to FIGS. 5-12, the head support 50 includes a base 52 and two arms 70. The base 52 is configured generally to connect each arm 70 to the first patient support 30. According to one embodiment of the invention, the base 52 includes a front wall 54, a rear wall 56, and a central member 58 extending between the front wall 54 and the rear wall 56. The central member 58 is joined to the front wall 54 and the rear wall 56 between a top edge 61 and a bottom edge 62 of each wall, 54 and 56, and extends generally between each side 63 of the front wall 54 and the rear wall 56. The central member 58 is generally planar with a channel 51 extending longitudinally along a center line 53 of the central member 58 between the front wall 54 and the rear wall 56.

The channel 51 is configured to receive a spine of the second antenna array 14. The channel 51 has a width, W, and extends from the front wall 54 toward the rear wall 56 for a length, L, suitable to receive the spine of the second antenna array 14. The cable connecting the second antenna array 14 to the second preamplifier module 24 extends out the front of the head support 50 and is routed to the second preamplifier module 24.

The front wall 54 includes a notch 55 extending from the top edge 61 of the front wall 54 to the depth of the channel 51 and for a width, W, of the channel 51. The channel preferably slopes from the front to the rear of the head support 50 complementary to the shape of the spine of the antenna array 14. The rear wall 56 may similarly include a notch 57 having a width, W, of the channel 51 and extending from a depth less than the depth of the notch in the front wall 54 and preferably above the height of the central member 58. Optionally, the channel 51 may be reversed such that the deepest portion of the channel extends out the rear wall 56 and slopes upward toward the front wall 54. As still another option, the channel 51 may have a substantially uniform depth and may accept the spine of the antenna array 14 in either orientation.

The base 52 further includes a plurality of ribs 60 extending laterally across the width of the central member 58. The ribs 60 protrude down from the central member 58 such that the bottom edges 62 of the front wall 54, rear wall 56, and each rib 60 extend a generally uniform distance below the central member 58 and are complementarily formed to a profile of the recess 35 in the first patient support 30.

Referring next to FIGS. 13-17, another embodiment of the base 52 and head support 50 is illustrated. The base 52 includes a front wall 54, a rear wall 56, and a central member 58 extending between the front wall 54 and the rear wall 56. A raised portion 65 extends longitudinally along the middle of the central member 58 between the front wall 54 and the rear wall 56 and is configured to support the riser 49. The raised portion 65, in combination with the riser 49, positions the second antenna array 14 and the contoured pad 47 generally in alignment with the first antenna array 12 to provide comfort and support for a patient extending between the first and second antenna arrays, 12 and 14. The base 52 is configured to mount within the second recess 35 of the first patient support 30. Any suitable alignment method may be used to position the base 52 within the second recess 35, including, but not limited to, tabs, posts or a recess complementary to the outer periphery of the base 52. A first and second pivot mount 160 extends along each side of the raised portion 65 and, in cooperation with a pivoting assembly 100, connects each arm 70 to the base 52. Optionally, the base 52 may be integrally formed with the first patient support 30.

Figure 18:
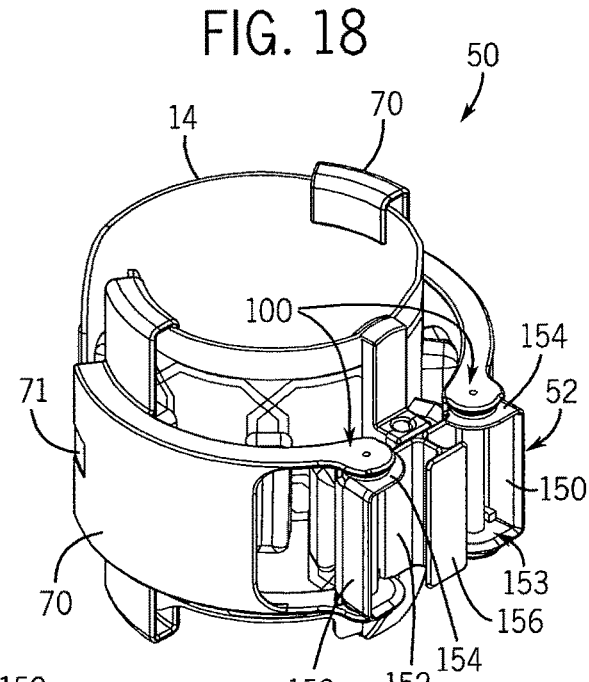
FIG. 18 is a perspective view from the end, side, and bottom of the curved patient support structure according to another embodiment of the invention.
Figure 19:
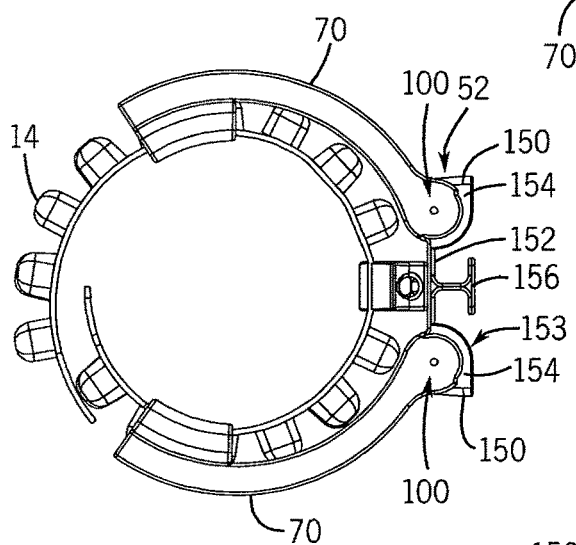
FIG. 19 is a side view of the curved patient support structure of FIG. 18.
Figure 20:
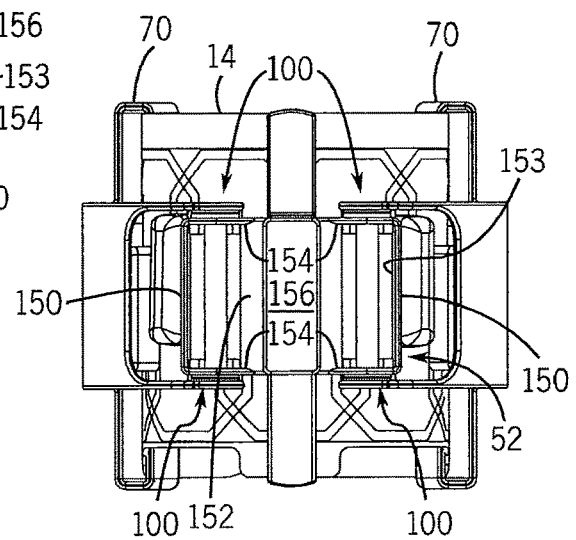
FIG. 20 is a bottom plan view of the curved patient support structure of FIG. 18.
Figure 21:
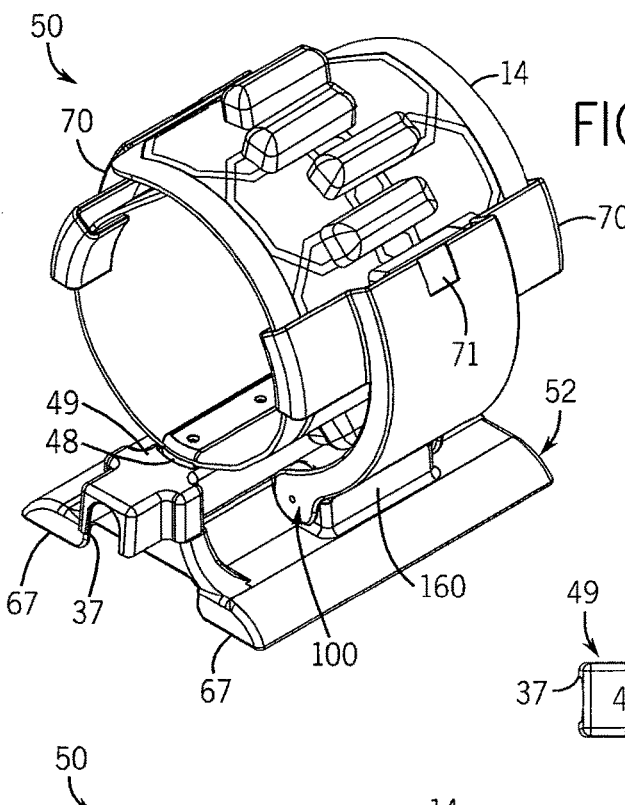
FIG. 21 is a perspective view of the curved patient support structure according to another embodiment of the invention.
Figure 22:
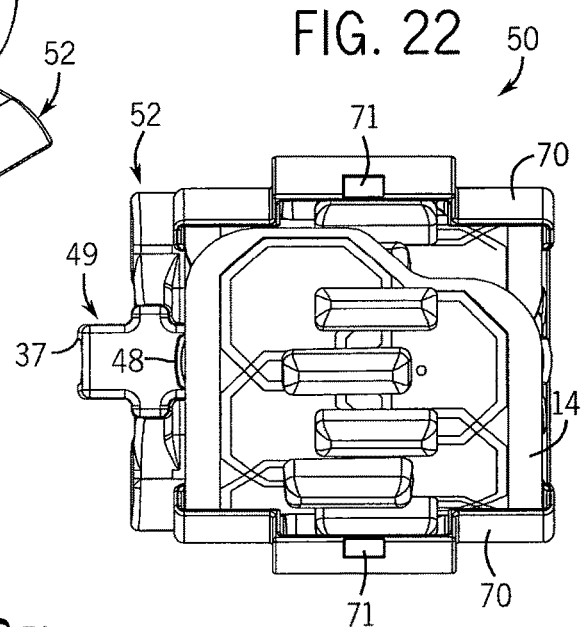
FIG. 22 is a top plan view of the curved patient support structure of FIG. 21.
Figure 23:
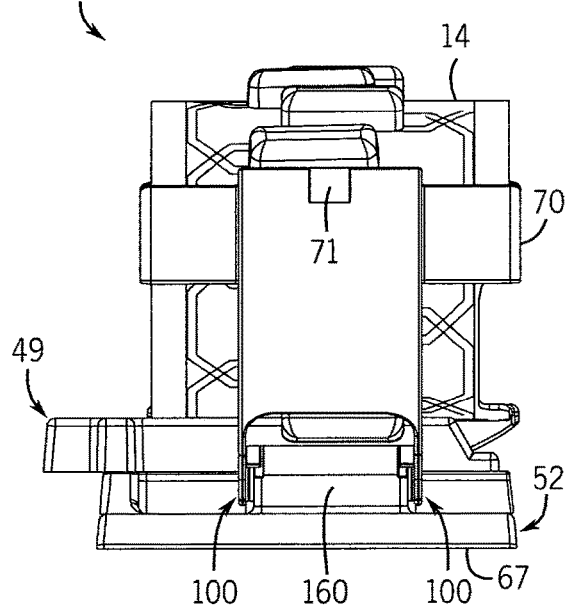
FIG. 23 is a side elevation view of the curved patient support structure of FIG. 21.

Referring next to FIGS. 18-20, another embodiment of the base 52 is illustrated. The base 52 includes a first end 150 and a second end 150 opposite the first end 150. A generally planar upper surface 152 extends between each of the first and second ends 150. Side portions 154 extend from each of the first and second ends 150 along a portion of the upper surface 152 but not to the center line of the upper surface 152, defining a space between the two side portions 154. Each side portion 154 extends a sufficient distance along the upper surface 152 such that the pivoting assembly 100 may connect each arm 70 to the base 52 at each side portion 154. Optionally, it is contemplated, that a solid side surface may extend between each 150 of the base 52. A cavity 153, generally open to a lower surface, is defined within the base 52 by the upper surface 152, first and second ends 150 and each side portion 154. A handle 156 is mounted to the interior side of the upper surface 152 and extends into the cavity 153. As illustrated, the handle 156 forms a "T" shape; however, it is contemplated that the handle 156 may be of any suitable shape. The handle 156 is preferably contained within the cavity 153 such that the base 52 may be placed within the second recess 35 of the first patient support. Optionally, the handle 156 may extend beyond the cavity 153 and the second recess 35 may be configured to receive the portion of the handle 156 extending beyond the cavity 153.

Figure 24:
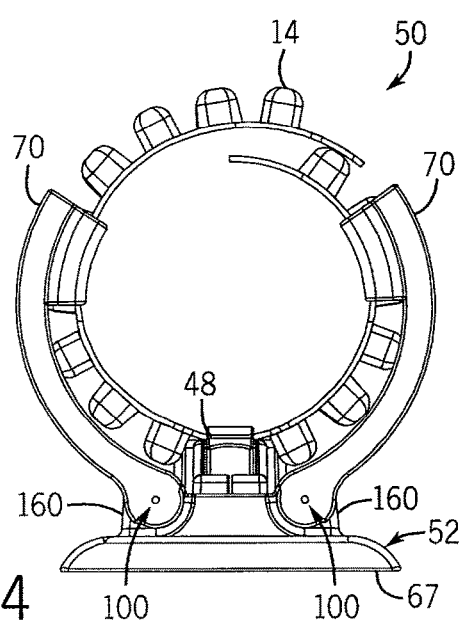
FIG. 24 is front elevation view of the curved patient support structure of FIG. 21.

Referring next to FIGS. 21-24, still another embodiment of the base 52 is illustrated. It is contemplated that the second support structure 50 may be used separately to support other anatomical regions, for example, arms or legs of adult patients during imaging. The base 52 is similar to the base 52 illustrated in FIGS. 13-17 except it has a wider footprint. The lower surface of the base 52 includes at least a first and a second generally planar surface 67. Optionally, the generally planar surface 67 may extend across the entire lower surface of the base 52, as shown in FIG. 24. Each of the first and second surfaces 67 extend out beyond the pivot mounts 160 to provide stability to the second support structure 50 as each arm 70 is moved to an open position. The planar lower surface 67 may be set directly on a table of the MRI scanner and the entire support structure 50 may be positioned on the table as needed to accommodate the desired anatomical region to be imaged.

A pivoting assembly 100 connects each arm 70 to the base 52. According to one embodiment of the invention, a first pivoting assembly 100 connects the arm 70 to the front wall 54 and a second pivoting assembly 100 connects the arm 70 to the rear wall 56 of the base 52. Both arms 70 connect to the base 52 proximate to the top edge 61 of the front and rear walls, 54 and 56 respectively. The first arm 70 is connected proximate to a first side 63 and the second arm 70 is connected proximate to the second side 63 of the base 52.

Referring also to FIGS. 12, and 29-32, one embodiment of the pivoting assembly 100 includes a clip 110, a cam 140, and a mounting boss 170. The clip 110 has an elongated body, having a first end 112, a second end 114, a thickness, and a width, Wc, greater than the thickness. A pair of arcuate members 120, or jaws, extend from the first end 112. Each arcuate member 120 first curves outward in a direction opposite from the other arcuate member 120 and then curves back inward toward the opposing arcuate member 120. According to one embodiment, each of the arcuate members 120 are symmetrical about a center line 130 extending axially from the first end 112 of the clip. The arcuate members 120 define an opening 122 therebetween configured to receive the cam 140. Each arcuate member 120 has an outer periphery 125 and an inner periphery 124. The inner periphery 124 includes one or more tabs 127 or recesses 128 configured to engage a complementary feature on the cam 140 and to define at least one desired spatial relationship between the cam 140 and the clip 110

The clip 110 farther includes a slot 132 in communication with the opening 122 defined by the arcuate members 120. The slot 132 extends from the opening 122 into the body of the clip 110. The slot 132 may be straight or curved and preferably extends along the center line 130 of the clip. The slot 132 permits the arcuate members 120 to be deflected apart and return to an unbiased position as the clip 110 is rotated about the cam 140. The force required to deflect the arcuate members 120 apart is a function of the length and width of the slot 132.

The clip 110 includes at least one locating hole 134 extending through the clip 110 proximate to the second end 114 of the clip 110. According to one embodiment of the invention, two locating holes 134 spaced apart along the length of the clip 110 are configured to receive a complementary boss 76 protruding from one of the arms 70. Two locating holes 134 prevent rotation of the arm 70 with respect to the clip 110. Optionally, a single locating hole 134 having a non-circular periphery may be used to both align the clip 110 to the arm 70 and prevent rotation. As still another option, the clip 110 may include one or more bosses which engage holes in the arm 70.

The cam 140 is designed to have an outer periphery 142 complementary to the opening 122 defined by the arcuate members 120 of the clip 110. The outer periphery 142 includes one or more tabs 144 or recesses 146 configured to engage the tabs 127 or recesses 128 of the inner periphery 124 of the opening 122 in the clip 110. One of the tabs 144 and/or recesses 146 defines a home position. A complementary tab 127 or recess 128 on the clip 110 engaging the tab 144 or recess 146 that defines the home position causes the arm 70 to be aligned in a preferred relationship to the base 52 to reduce image artifacts resulting from overlapping loops in the antenna array 14.

The cam 140 is mounted in a fixed relationship to the base 52 of the head support 50. An opening 148 in the cam 140 engages the boss 170 protruding from the base 52. Optionally, the cam 140 may have a boss which engages an opening in the base 52. The opening 148 is non-circular to prevent rotation of the cam 140 with respect to the base 52. The opening 148 may also be non-symmetric such that the orientation of the boss 170 defines the angular orientation of the cam 140 to the base 52.

Referring next to FIGS. 38-39, a pivoting assembly connects each arm 70 along a side edge of the central member 58. Referring also to FIGS. 40-44, the pivoting assembly is a hinge 200 having a first leaf 202 and a second leaf 204. Each of the first leaf 202 and the second leaf include at least one mounting hole 205 configured to receive a securing member, such as a screw or a bolt, to mount the respective leaf to either the arm 70 or the base 52. Each of the first leaf 202 and the second leaf 204 include at least one barrel section 206 connected along an edge of the leaf, 202 or 204. Each barrel section 206 is generally cylindrical, has a hollow interior 208, and is uniform in size to the other barrel sections 206. The first leaf 202 and the second leaf 204 are positioned adjacent to each other such that the barrel sections 206 on the first leaf 202 align with the barrel sections 206 on the second leaf 204, defining a chamber 210 having a first end 211 and a second end 212 into which a central assembly 220 may be inserted.

The central assembly 220 is configured to provide a variable resistance to pivoting the hinge 200. The assembly 220 includes a first insert 230 and a second insert 240 which define a first end 232 and a second end 242, respectively, of the assembly 220. Each insert, 230 and 240, has a generally smooth outer periphery having a diameter configured to slidably engage the chamber 210 defined by the barrel sections 206. The first end 232 of the assembly 220 extends generally to the first end 211 of the chamber 210 and the second end 242 of the assembly 220 extends generally to the second end 212 of the chamber 210.

The first insert 230 includes a generally cylindrical cavity 235 extending through at least a portion of the first insert 230. A first end 234 of the first insert 230, proximate to the first end 211 of the chamber 210, may be a wall and define a stop for a pin 250 inserted into the central assembly 220. Optionally, a flange or other protrusion may extend into the cavity 235 to define the stop. The first insert 230 extends for a distance from the first end 211 into the chamber 210. The thickness of a wall of the first insert 230 is defined by the diameter of the outer periphery and the diameter of the cylindrical cavity 235.

The second insert 240 includes a generally cylindrical cavity 245 extending through the second insert 240. A first end 244 of the second insert 240 is proximate to the second end 212 of the chamber 210, and the second insert 240 extends for a distance from the second end 212 into the chamber 210. A gap 216 is defined within the chamber 210 between the first insert 230 and the second insert 240. At least a portion 241 of the cavity 245 is threaded. The thickness of a wall of the second insert 240 is defined by the diameter of the outer periphery and the diameter of the cylindrical cavity 245 and is preferably the same thickness as the wall of the first insert 230.

The pin 250 is configured to engage both the first insert 230 and the second insert 240. A first end 252 of the pin 250 slidably engages the cavity 235 of the first insert 230, and a threaded portion 256 of the pin 250, proximate to a second end 254 of the pin 250, engages the threaded portion 241 of the second insert 240. The second end 254 of the pin 250 includes a recess 255 configured to accept a tool, for example a screw driver or box-head wrench, to rotate the pin 250. As the pin 250 is rotated, the threaded portion 256 causes the pin 250 to move axially within the first and second inserts, 230 and 240 respectively. The pin 250 includes a flange 258 extending around the periphery of the pin 250. The flange 258 has a thickness equal to or less than the thickness of the second insert 240 and is configured to engage the end of the second insert 240 within the chamber 210. Multiple washers 260 and o-rings 270 are alternately disposed along the outer periphery of the pin 250 to substantially fill the gap 216 between the first insert 230 and the second insert 240.

Referring next to FIGS. 33-36, each arm 70 is preferably symmetric about a center line 75 such that the same arm 70 may be mounted to either side of the base 52 by rotating the arm 70 about the center line 75 to reverse its orientation. In a first embodiment of the invention, the arm 70 includes a first curved member 78 and a second curved member 80, each curved member, 78 and 80, extending from a first end 72 to a second end 74 of the arm 70. A front face 82 of the arm 70 is joined to a first curved side face 84 of the arm 70 along a front edge 83 to generally define the first curved member 78. A rear face 86 of the arm 70 is joined to a second curved side face 88 of the arm 70 along a rear edge 87 to generally define the second curved member 80.

Each of the front and rear faces, 82 and 86 respectively, extends beyond the respective side face, 84 and 88, at the first end 72 of the arm 70 and is configured to receive the clip 110 of the pivoting assembly 100. The portion of each of the front and rear faces, 82 and 86 respectively, proximate to the first end 72 is curved complementary to the arcuate members 120 of the clip 110. A mounting hole 90 extends through each of the front and rear faces, 82 and 86 respectively, within the curved portion, to receive a fastener, for example, a screw or a bolt, which positively retains the arm 70 to the mounting boss 170 of the pivoting assembly 100. At least one boss 76 protrudes from the interior surface of each of the front and rear faces, 82 and 86 respectively, toward the other of the front and rear faces to engage each of the locating holes 134 in the clip 110.

The interior surface of the front and rear faces, 82 and 86 respectively, further includes a curved retaining surface, 92 and 94 respectively. Each curved retaining surfaces, 92 and 94, is spaced apart from the first or second curved side face, 84 or 88 respectively, defining a channel, 93 and 95, configured to receive the second antenna array 14.

Each arm 70 further includes at least one support member 96 extending between the first curved member 78 and the second curved member 80. In one embodiment of the invention, a first support member 96 extends between the curved members, 78 and 80, proximate to the first end 72 of the arm 70 and a second support member 96 extends between the curved members, 78 and 80, proximate to the second end 74 of the arm 70. A space 97 defined by interior edges of each of the support members 96 and the curved members, 78 and 80, provides a line of sight and permits access to a patient through the arm 70.

Another embodiment of the arm 70 is illustrated in FIGS. 45-46. Each arm 70 is preferably symmetric about a center line 75 such that the same arm 70 may be mounted to either side of the base 52 by rotating the arm 70 about the center line 75 to reverse its orientation. The arm 70 includes a central curved member 79 joined to a front face 82 along a front edge 83 and joined to a rear face 86 along a rear edge 87. Each of the front face 82, central curved member 79, and rear face, 86 extend from the second end 74 of the arm 70. Each of the front face 82 and rear face 86 extend to the first end 72 of the arm 70 with the central curved member 79 extending along only a portion of the distance between the second and first ends, 74, 72. The width of each of the front and rear face 82, 86 is preferably equal to or greater than the width of a pickup assembly on the antenna array 14, thereby defining a channel 77 between the front face 82, central curved member 79, and the rear face 86 configured to receive the pickup assemblies of the second antenna array 14. Each of the front face 82 and rear face 86 also includes a mounting hole 90, extending through each face, 82 and 86, to receive a fastener, for example, a screw or a bolt, which positively retains the arm 70 to one of the pivot mounts 160. Proximate the second end 74 of the arm, a recess 71 may be included to receive one side of a hook and loop fastener. A strap (not shown) made up of the other side of the hook and loop fastener may engage the fastener on one arm 70 and extend over the antenna array 14 to engage the fastener on the other arm 70.

A pair of retention members 400 extend from each of the front face 82 and the rear face 86 proximate to the second end 74 of the arm. Each retention member 400 includes a first surface 402 connected to either the front face 82 or the rear face 86 along at least a portion of the interior edge 401 of the face. The first surface 402 extends away from each respective face 82, 86 to an outer surface 404 of the retention member 400. The outer surface 404 extends between the first surface 402 and a retaining surface 406 which is generally parallel to the first surface, forming a channel 405 defined by the first surface 402, the outer surface 404, and the retaining surface 406. Each of the first surface 402, outer surface 404, retaining surface 406, and the channel 405 defined therein are generally curved, corresponding to the curvature of the central member 79 of the arm 70. Each retention member 400 is configured to receive a portion of the second antenna array 14 therein.

A pair of washers 420, 430 may be inserted between the interior surface of each of the front 82 and rear face 86 where they engage the pivot mount 160. A boss 415 on the interior surface is positioned such that the mounting hole 90 extends therethrough. The boss is preferably has a non-circular periphery and is complementary to an inner periphery 422, 432 of each washer 420, 432 respectively. The non-circular periphery prevents rotation of the washers 420, 432 as the arm 70 is moved between a first position and a second position. According to one embodiment of the invention, the first washer 420 may be made of viton and the second washer 430 may be made of nylon. Optionally, other materials may be used. As a fastener connects each arm 70 to the pivot mount 160, the washers 420, 430 are compressed generating a friction force resisting rotation of the arm 70 about the pivot. Application of a force to the arm 70 of sufficient magnitude to overcome the resistance causes rotation of the arm 70 in the direction of the applied force. When the force is removed, the friction force is of sufficient magnitude to retain the arm at its current point at or between, the first and second positions.

According to another embodiment of the invention, shown in FIGS. 38-39, each of the hinges 200 connects the arm 70 along a side edge of the central member 58. A first hinge 200 connects the first side face 84 to the central member 58 proximate to one of the front wall 54 and the rear wall 56 and, a second hinge 200 connects the second side face 88 to the central member 58 proximate to the other of the front wall 54 and the rear wall 56. The portion of each of the front and rear faces, 82 and 86 respectively, proximate to the first end 72 extends generally contiguous with the respective side face, 84 and 88.

Referring next to FIGS. 37-38, the second end of one of the arms 70 may be configured to receive a clip 110 or a hinge 200. A second arm 70 may then be connected on each side of the head support 50, providing a second pivot point for each arm. The combination of two arms 70 on each side permits a larger coil array 14 to be used with the head support 50.

Referring next to FIGS. 25-28, still another embodiment of the patient support structure 300, which is configured to hold an antenna array 14 around a shoulder, is illustrated. The patient support structure 300 includes a first arm 302 and a second arm 304 connected by friction hinges 200 to a base 52. The base 52 includes a channel 51 configured to receive the spine of an antenna array 14, thereby positioning the antenna array 14 on the shoulder. The first arm 302 is configured to extend down the chest of the patient and the second arm 304 is configured to extend down the back of the patient. Each arm 302,304 holding the antenna array 14 against the patient.

In operation, the modularity of the patient support assembly 10 permits the assembly to be configured for imaging the back of a patient, the head of a patient, or both simultaneously. The first antenna array 12 is placed within the first recess 31 if back and/or spine imaging is desired and the head support 50 and second antenna array 14 is placed in the second recess 35 if head imaging is desired. If included, the corresponding preamplifier modules, 22 or 24, are also inserted into the patient support assembly 10, and a patient may be placed on the assembly 10 for imaging. Each of the antenna arrays, 12 or 14, is configured to detect nuclear magnetic resonance (NMR) signals resulting from the magnetic field generated by the MRI scanner. The NMR signals are transferred from each antenna array, 12 or 14, via the connecting cable to the corresponding preamplifier module, 22 or 24, and subsequently to the MRI scanner to generate a desired image. Optionally, if the electronic circuits of the preamplifier modules, 22 and 24, are incorporated into the respective antenna arrays, 12 and 14, the connecting cables may be configured to interface directly with the MRI scanner.

Figure 9:
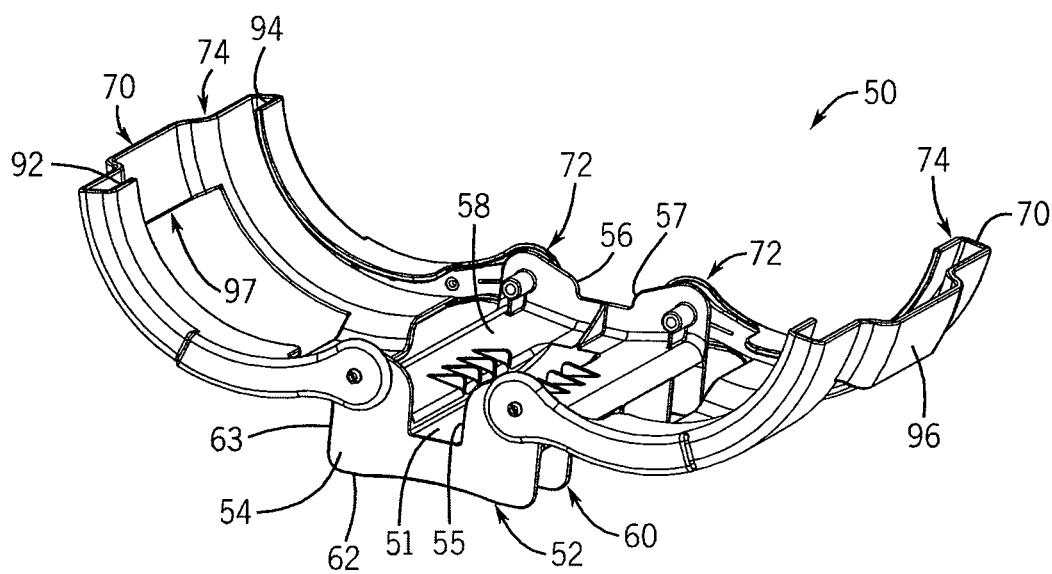
FIG. 9 is a perspective view of the curved patient support structure used in the patient support structure of FIG. 1 shown in a open position.
Figure 10:
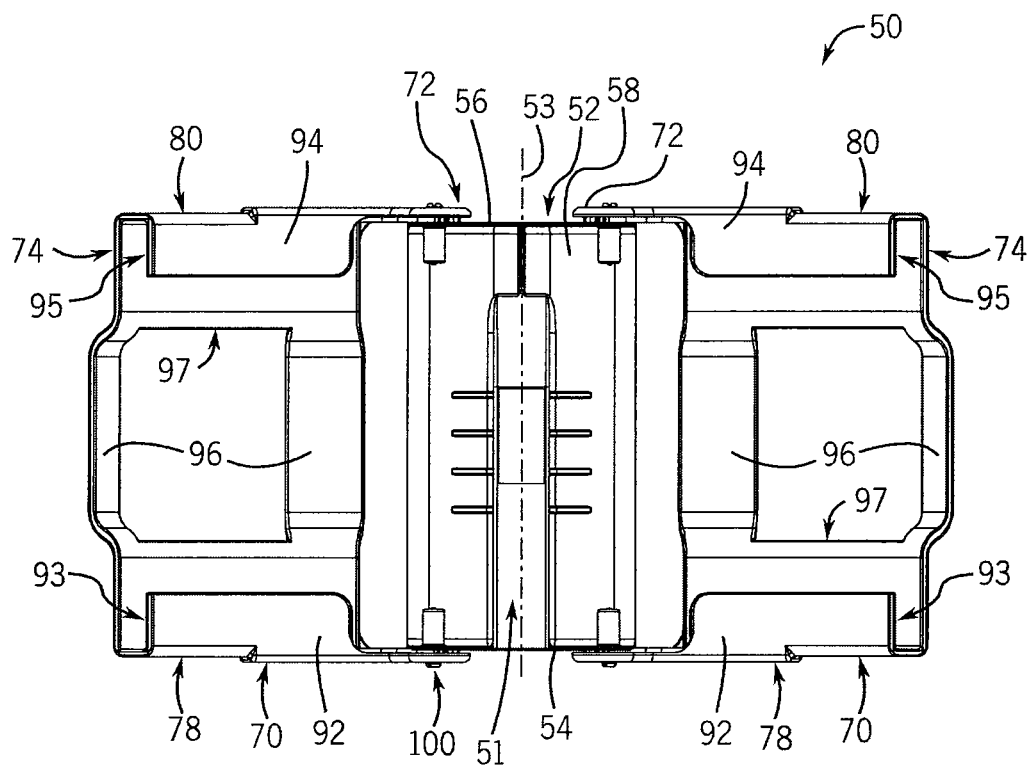
FIG. 10 is a top plan view of the curved patient support structure of FIG. 9.
Figure 11:
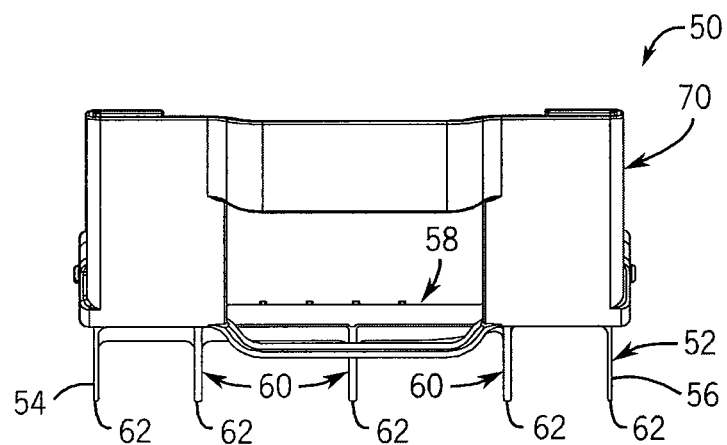
FIG. 11 is a side elevation view of the curved patient support structure of FIG. 9.
Figure 12:
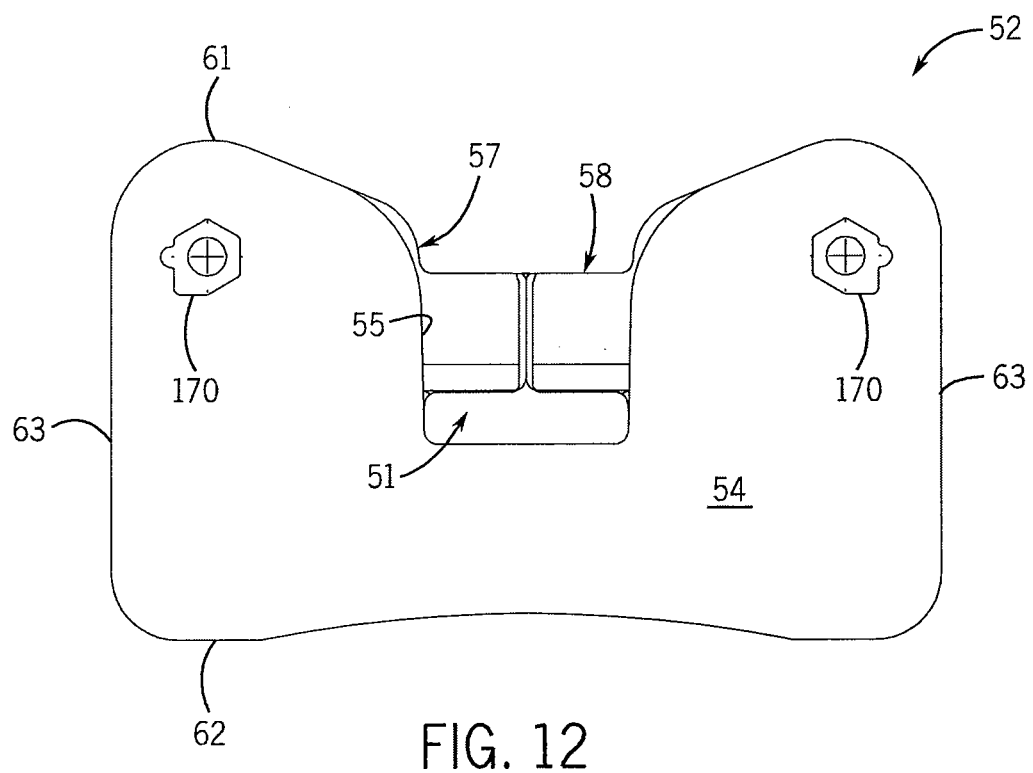
FIG. 12 is a front elevation view of a base of the curved patient support structure of FIG. 5.
Figure 13:
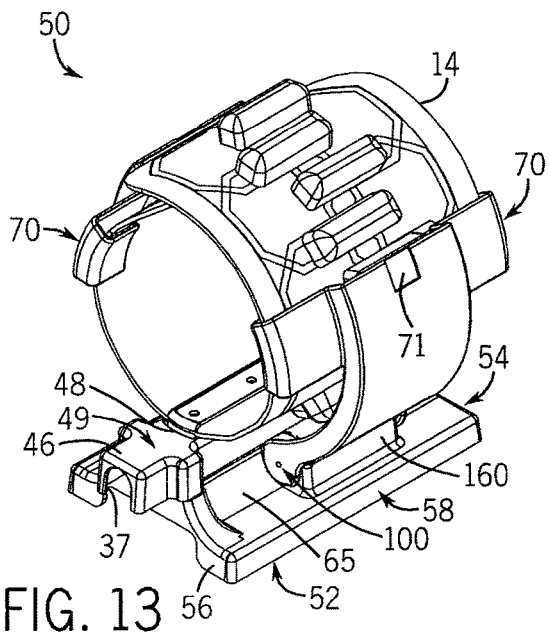
FIG. 13 is a perspective view from the top, rear, and side of the curved patient support structure used in the patient support structure of FIG. 3 shown in a home position.
Figure 14:
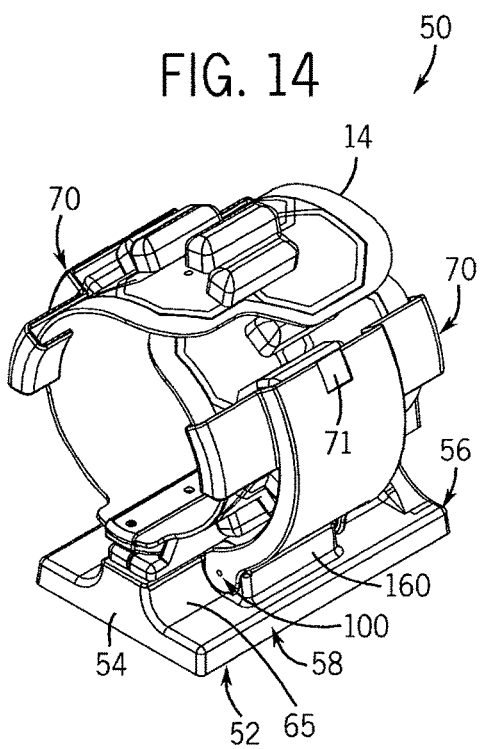
FIG. 14 is a perspective view from the top, front, and side of the curved patient support structure used in the patient support structure of FIG. 3 shown in a home position.
Figure 15:
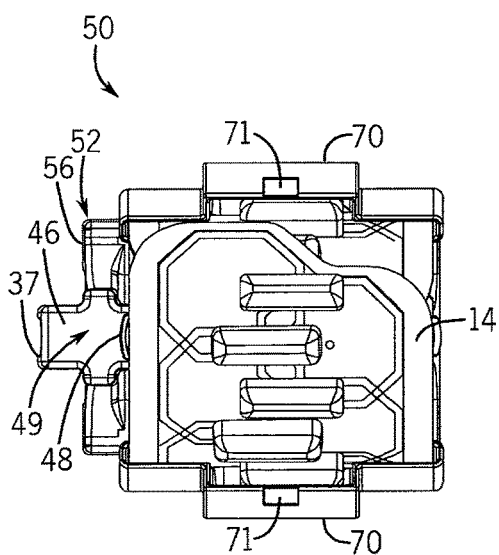
FIG. 15 is a top plan view of the, curved patient support structure of FIG. 13.
Figure 16:
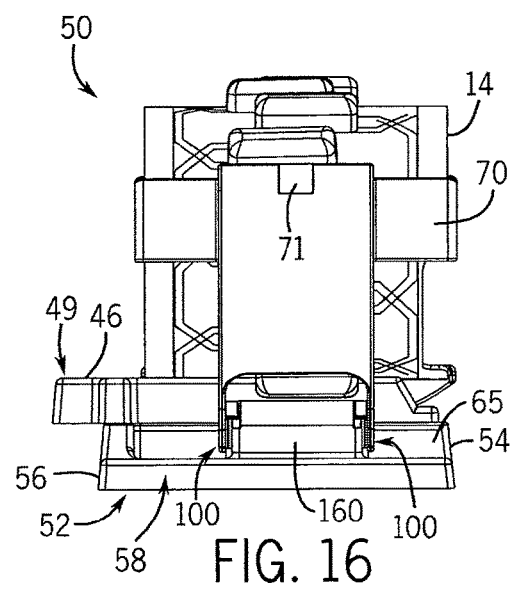
FIG. 16 is a side elevation view of the curved patient support structure of FIG. 13.
Figure 17:
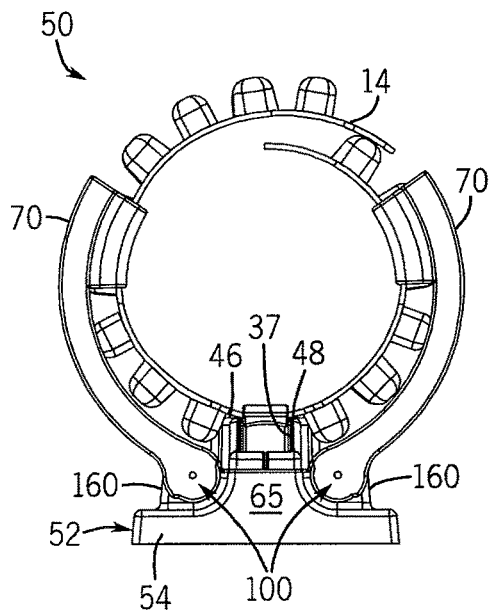
FIG. 17 is front elevation view of the curved patient support structure of FIG. 13.

If a patient's head is to be imaged, the arms 70 of the head support 50 may be rotated outward to an open position, see FIG. 9, in order to receive the patient. This permits easy placement and alignment of the patient within the head support 50, particularly if the patient requires medical incubation and ventilation. Once the patient has been positioned, the arms 70 may be rotated back to the home position, see FIG. 5, to perform the imaging.

Rotation between the home position and the open position, or optionally, other angular positions, is facilitated by the pivoting assembly 100. According to a first embodiment of the invention, one of the tabs 127 or recesses 128 on the clip 110, along with a corresponding tab 144 or recess 146 on the cam 140, defines the home position. For example, a tab 127 on the clip 110 engages a recess 146 on the cam 140 to positively retain the clip 110, and consequently the arm 70 connected to the clip 110 in the home position. Rotating the arm 70 from the home position requires the arcuate members 120 on the clip 110 to be biased apart from each other such that the space between the ends of the arcuate members 120 is sufficient to permit the tab 127 to disengage from the recess 146. Once the tab 127 has disengaged from the recess 146, the arcuate members 120 return to an unbiased state to permit rotation of the arm 70. Optionally, the cam 140 may be configured to such that the arcuate members 120 remain in a biased state requiring some force to rotate the arm 70.

The arm 70 is then rotated to the open position. The open position may be defined by a second recess 146 on the cam 140. The tab 127 may consequently engage the second recess 146 and positively retain the arm 70 in the open position. Optionally, multiple tabs 127 positioned along the inner periphery of the arcuate members 120 may define multiple angular positions at which the arms 70 may be aligned. As still another option, a stop 145 may protrude from the outer periphery of the cam 140. The arm 70 is then permitted to rotate until the tab 127 on the clip 110 engages the stop 145 on the cam 140.

According to another embodiment of the invention, the arm 70 may include a stop member 440 along the inner surface of each of the front face 82 and rear face 86 proximate to the first end 72 of the arm 70. The stop member 440 includes a first end 442 which engages a complementary stop member mounted, for example and the face of the pivot mount 160. Optionally, the first end 442 may engage the raised portion 65 of the base 52, restricting further rotation toward the center of the patient support 50, defining the home position. The stop member 440 also includes a second end 444 which engages a complementary stop member mounted, for example and the face of the pivot mount 160. Optionally, the second end 444 engages the upper surface of the base 52, restricting further rotation away from the center of the patient support 50, defining the open position.

After positioning the patient, the arm 70 may be returned to the home position by reversing the steps described above. When the arm 70 returns to the home position, the arcuate members 120 on the clip 110 must again be biased apart from each other such that the space between the ends of the arcuate members 120 is sufficient to permit the tab 127 to engage the recess 146. The action of the arcuate members 120 provides both a tactile sensation to the operator as well as an audible click such that the operator is aware that the arm 70 is in the home position. Similarly, the tactile sensation and/or the audible click may indicate alignment of the arm 70 in any of the other desired positions corresponding to the recesses 146 on the cam 140. The force required to pivot the arm 70 may be varied by adjusting the length and/or width of the slot 132 in the clip 110 according to the requirements of each application.

According to another embodiment of the present invention, the hinge 200 permits torque adjustment for pivoting the arm 70 about the base 52. The torque adjustment is achieved by inserting a tool into the recess 255 on the pin 250 and rotating the pin 250 into the first insert 230. As the pin 250 is rotated, the threaded portion 256 of the pin 250 engages the threaded portion 241 of the second insert 240 to cause the pin 250 to move axially toward the first insert 230. The flange 258 applies a force to the washers 260 and o-rings 270 located in the gap 216 between the first insert 230 and the second insert 240. This force causes the o-ring 270 volume to displace toward the inner periphery of the chamber 210. The increased interference between the o-rings 270 and the chamber 210 result in an increased torque to rotate the arm 70. The radial torque can be adjusted by the end user or set to a preferred force during assembly.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A patient support structure for supporting an anatomical region of a patient and for positioning a flexible antenna array with respect to the anatomical region while obtaining a Magnetic Resonance Image (MRI), the patient support structure comprising:
- a base including:
  - a first end,
  - a second end opposite the first end,
  - a first side,
  - a second side opposite the first side, wherein each of the first and second sides extend between the first and second ends,
  - at least one first mounting surface proximate to the first side of the base, and
  - at least one second mounting surface proximate to the second side of the base;
- a first arm having a first end proximate to the base and a second end distal from the base, the first arm including:
  - at least one third mounting surface pivotally connected to the at least one first mounting surface, wherein the first arm is movable between a first position and a second position, and
  - at least one first antenna guide configured to slidably engage the flexible antenna array as the first arm moves between the first and second positions, wherein the flexible antenna array includes a plurality of antenna coils and a flexible housing to which each of the plurality of antenna coils is mounted; and
- a second arm having a first end proximate to the base and a second end distal from the base, the second arm including:
  - at least one fourth mounting surface pivotally connected to the at least one second mounting surface, wherein the second arm is movable between a first position and a second position, and
  - at least one second antenna guide configured to slidably engage the flexible antenna array as the second arm moves between the first and second positions.

2. The patient support structure of claim 1 further comprising:
- a first friction mount pivotally connecting the at least one third mounting surface of the first arm to the at least one first mounting surface proximate to the first side of the base; and
- a second friction mount pivotally connecting the at least one third mounting surface of the second arm to the at least one third mounting surface proximate to the second side of the base.

3. The patient support structure of claim 1 wherein the base further includes a channel extending between the first and second ends and configured to receive a member protruding from a surface of the antenna array.

4. The patient support structure of claim 1 further comprising a riser block extending longitudinally between the first and second ends of the base and extending away from the base between the first and second arms, wherein the riser block engages the antenna array to position the antenna array between the first and second arms.

5. The patient support structure of claim 1 wherein the base further includes a planar lower surface.

6. The patient support structure of claim 1 wherein the base further includes:
- an upper surface extending between the first end, the second end, the first side and the second side, the upper surface having a first side facing the first and second arms and a second side opposite the first side;
- a handle protruding from the second side of the upper surface into a cavity defined by the first end, the second end, the first side, the second side and the upper surface.

7. The patient support structure of claim 1 wherein the first antenna guide for the first arm and the second antenna guide for the second arms each includes:
- a first retention member proximate to the second end of the respective arm extending outwardly from the arm toward the first end of the base, and
- a second retention member proximate to the second end of the respective arm extending outwardly from the toward the second end of the base.

8. The patient support structure of claim 7 wherein each retention member comprises:
- a first surface extending from the first or second arm;
- a retaining surface, offset from and generally parallel to the first surface; and
- an outer surface connecting the distal edge of each of the first surface and the retaining surface, wherein a channel is formed by the first surface, retaining surface, and outer surface, the channel slidably engaging the antenna array.

9. A patient support structure for supporting an anatomical region of a patient and for positioning a flexible antenna array with respect to the anatomical region while obtaining a Magnetic Resonance Image (MRI), the patient support structure comprising:
- a base including:
  - a first end,
  - a second end opposite the first end,
  - a first side,
  - a second side opposite the first side, wherein each of the first and second sides extend between the first and second ends,
  - at least one mounting surface proximate to the first side of the base, and
  - at least one mounting surface proximate to the second side of the base;
- a first arm having a first end proximate to the base and a second end distal from the base, the first arm including:
  - at least one mounting surface pivotally connected to the at least one mounting surface proximate to the first side of the base, wherein the first arm is movable between a first position and a second position,
  - at least one first antenna guide configured to slidably engage the flexible antenna array, and
  - an arcuate central support member; and
- a second arm having a first end proximate to the base and a second end distal from the base, the second arm including:
  - at least one mounting surface pivotally connected to the at least one mounting surface proximate to the second side of the base, wherein the second arm is movable between a first position and a second position,
  - an arcuate central support member, and
  - at least one second antenna guide configured to slidably engage the flexible antenna array, wherein the at least one first antenna guide of the first arm and the at least one second antenna guide of the second arm each include a first retention member extending outward in a first direction from a center axis of the arcuate central support member proximate to the second end of the respective arm and a second retention member extending outward in a second direction, opposite the first direction, from the center axis of the arcuate central support member proximate to the second end of the respective arm.

10. The patient support structure of claim 9 wherein the first and second retention members of the first and second arms each define a channel extending along the end of the retention member distal from the center axis of the arcuate central support member and extending generally parallel to the arcuate central support member.

11. A patient support structure for supporting an anatomical region of a patient and for positioning a flexible antenna array with respect to the anatomical region while obtaining a Magnetic Resonance Image (MRI), the patient support structure comprising:
a base including:
a first end,
a second end opposite the first end,
a first side,
a second side opposite the first side, wherein each of the first and second sides extend between the first and second ends,
at least one mounting surface proximate to the first side of the base, and
at least one mounting surface proximate to the second side of the base;
a first arm having a first end proximate to the base and a second end distal from the base, the first arm including:
at least one mounting surface pivotally connected to the at least one mounting surface proximate to the first side of the base, wherein the first arm is movable between a first position and a second position, and
at least one first antenna guide configured to slidably engage the flexible antenna array, wherein the first antenna guide of the first arm includes a first channel extending along at least a portion of a first side of the first arm and a second channel extending along at least a portion of a second side of the first arm; and
a second arm having a first end proximate to the base and a second end distal from the base, the second arm including:
at least one mounting surface pivotally connected to the at least one mounting surface proximate to the second side of the base, wherein the second arm is movable between a first position and a second position, and
at least one second antenna guide configured to slidably engage the flexible antenna array, wherein the second antenna guide of the second arm includes a first channel extending along at least a portion of a first side of the second arm and a second channel extending along at least a portion of a second side of the second arm.

12. A patient support structure for supporting an anatomical region of a patient and for positioning a flexible antenna array with respect to the anatomical region while obtaining a Magnetic Resonance Image (MRI), the patient support structure comprising:
a base;
a flexible antenna array including a plurality of antenna coils and a flexible housing to which each of the plurality of antenna coils is mounted;
a first arm movable between a first position and a second position, the first arm including a first retention means for holding the flexible antenna array along an inner periphery of the first arm as the first arm moves between the first and second positions, wherein the flexible antenna array slidably engages the first retention means, as the first arm moves between the first position and the second position;
a second arm movable between a first position and a second position, the second arm including a second retention means for holding the flexible antenna array along an inner periphery of the second arm as the second arm moves between the first and second positions, wherein the flexible antenna array slidably engages the second retention means as the second arm moves between the first position and the second position;
a first friction mounting means for pivotally connecting the first arm to the base; and
a second friction mounting means for pivotally connecting the second arm to the base.

* * * * *